United States Patent
Strasburger et al.

(10) Patent No.: US 7,807,154 B2
(45) Date of Patent: Oct. 5, 2010

(54) LEPTIN ANTAGONIST AND METHOD FOR QUANTITATIVE MEASUREMENT OF LEPTIN

(75) Inventors: Christian J. Strasburger, Berlin (DE); Martin Bidlingmaier, München (DE); Zida Wu, Berlin (DE); Guiseppe Matarese, Naples (IT); Richard J. M. Ross, Sheffield (GB)

(73) Assignee: Biofusion Licensing Limited, Sheffield (GB)

(*) Notice: Subject to any disclaimer, the term of this patent is extended or adjusted under 35 U.S.C. 154(b) by 755 days.

(21) Appl. No.: 10/579,203

(22) PCT Filed: Nov. 17, 2004

(86) PCT No.: PCT/EP2004/013043

§ 371 (c)(1),
(2), (4) Date: Feb. 27, 2007

(87) PCT Pub. No.: WO2005/049655

PCT Pub. Date: Jun. 2, 2005

(65) Prior Publication Data

US 2008/0118503 A1    May 22, 2008

(30) Foreign Application Priority Data

Nov. 17, 2003   (DE)   .................. 103 53 593

(51) Int. Cl.
*A61K 39/395* (2006.01)
*C07K 16/28* (2006.01)
*C07K 16/46* (2006.01)

(52) U.S. Cl. .............. 424/130.1; 424/133.1; 424/134.1; 424/135.1; 424/136.1; 424/143.1; 424/179.1; 530/387.1; 530/388.22; 530/391.1

(58) Field of Classification Search .................. None
See application file for complete search history.

(56) References Cited

U.S. PATENT DOCUMENTS 7,446,183 B2 * 11/2008 Ross et al. .................. 530/399

FOREIGN PATENT DOCUMENTS

WO    WO 99/59614   * 11/1999

* cited by examiner

*Primary Examiner*—Jeffrey Stucker
*Assistant Examiner*—Stephen Gucker
(74) *Attorney, Agent, or Firm*—Kening Li; Pinsent Masons LLP

(57) ABSTRACT

Antibody A or a fusion protein thereof specifically binding to a leptin receptor (leptin-R) or a leptin-binding protein (leptin-BP), as well as compositions and methods for the use of these antibodies or fusion proteins for quantitative analysis, for therapeutic purposes and for the preparation of therapeutic drugs. Also disclosed is a method for quantitative determination of leptin in a sample of solubilized or suspended leptin-binding proteins by using specific antibodies or fusion proteins according to the invention, as well as diagnostic agents and (diagnostic) kits containing this antibody or fusion protein.

20 Claims, 20 Drawing Sheets

XHNPIPMPPAAAGLLLLAAQPAMAELVMTQSPKFMSTSIGDRVNITCKAT
QNVRTAVTWYQQKPGQSPQALIFLASNRHTGVPARFTGSGSGTDFTLTIN
NVKSEDLADYFCLQHWNYPLTFGSGTKLEIKRADAAPTVSIFPPSSEQLT
SGGASVVCFLNNFYPKDINVKWKIDGSERQNGVLNSWTDQDSKDSTYSMS
STLTLTKDEYERHNSYTCEATHKTSTSPIVKSFNRGEC**SRVKRXQSXG
GPGTPIRPIGXPYYNSLGGGFQ

```
DNA: NANGTCATAATCCAATACCTATGCCTACGGCAGCCGCTGGATTGTTATTAC
 +3:   X  H  N  P  I  P  M  P  T  A  A  A  G  L  L  L  L
       pComb3 vector        SacI    V_L(κ) primer
DNA: TCGCTGCCCAACCAGCCATGGCCGAGCTCGTGATGACCCAGTCTCCAAAAT
 +3:   A  A  Q  P  A  M  A  E  L  V  M  T  Q  S  P  K  F DNA: TCATGTCCACATCAATAGGAGACAGGGTCAATATCACCTGCAAGGCCACTC
 +3:   M  S  T  S  I  G  D  R  V  N  I  T  C  K  A  T  Q DNA: AGAATGTTCGTACTGCTGTTACCTGGTATCAACAGAAACCAGGGCAGTCTC
 +3:   N  V  R  T  A  V  T  W  Y  Q  Q  K  P  G  Q  S  P DNA: CTCAAGCACTGATTTTCTTGGCATCCAACCGGCACACTGGTGTCCCTGCTC
 +3:   Q  A  L  I  F  L  A  S  N  R  H  T  G  V  P  A  R DNA: GATTCACAGGCAGTGGATCTGGGACAGATTTCACTCTCACCATTAACAATG
 +3:   F  T  G  S  G  S  G  T  D  F  T  L  T  I  N  N  V DNA: TGAAATCTGAAGACCTGGCAGATTATTTCTGTCTACAACATTGGAATTATC
 +3:   K  S  E  D  L  A  D  Y  F  C  L  Q  H  W  N  Y  P DNA: CTCTCACGTTCGGCTCGGGGACAAAGTTGGAAATAAAACGGGCTGATGCTG
 +3:   L  T  F  G  S  G  T  K  L  E  I  K  R  A  D  A  A DNA: CACCAACTGTATCCATCTTCCCACCATCCAGTGAGCAGTTAACATCTGGAG
 +3:   P  T  V  S  I  F  P  P  S  S  E  Q  L  T  S  G  G DNA: GTGCCTCAGTCGTGTGCTTCTTGAACAACTTCTACCCCAAAGACATCAATG
 +3:   A  S  V  V  C  F  L  N  N  F  Y  P  K  D  I  N  V DNA: TCAAGTGGAAGATTGATGGCAGTGAACGACAAAATGGCGTCCTGAACAGTT
 +3:   K  W  K  I  D  G  S  E  R  Q  N  G  V  L  N  S  W
           BclI
DNA: GGACTGATCAGGACAGCAAAGACAGCACCTACAGCATGAGCAGCACCCTCA
 +3:   T  D  Q  D  S  K  D  S  T  Y  S  M  S  S  T  L  T DNA: CGTTGACCAAGGACGAGTATGAACGACATAACAGCTATACCTGTGAGGCCA
 +3:   L  T  K  D  E  Y  E  R  H  N  S  Y  T  C  E  A  T
                                                     C_L(κ) primer
DNA: CTCACAAGACATCAACTTCACCCATTGTCAAGAGCTTCAACAGGGGAGAGT
 +3:   H  K  T  S  T  S  P  I  V  K  S  F  N  R  G  E  C
       Stop   XbaI         NotI              KpnI
DNA: GTTAGTAATCTAGAGTTAAGCGGCCGCAATCGAGGGGGGGCCCGGTACCCC
 +3:   *  *  S  R  V  K  R  P  Q  S  R  G  G  P  V  P  Q DNA: AATTCGCCCTATAGGGGNGCCGTATTACAATTCACTGGGCGGCGGTTTTCA
 +3:   F  A  L  *  G  X  R  I  T  I  H  W  A  A  V  F  X

DNA: AN
 +3:
```

Figure 2

LAXRGGGRKIXFXRETVIMKYLXAYGPAAGLLLLAAQPAMAQVKLLESGP
GLVAPSESLSITCTISGFSLTDDGVSWIRQPPGKGLEWLGVIWGGGSTYF
NSLFKSRLSITRDNSKSQVFLEMDSLQTDDTAMYYCAKHDGHETMDYWGQ
GTSVTVSSSKTTPPSVYPLAPGSAAQTNSMVTLGCLVKGYFPEPVTVTWN
SGSLSSGVHTFPAVLQSDLYTLSSSVTVPSSTWPSETVTCNVAHPASSTK
VDKKIVPRDCTSHHHHHH*ASLVVAVALHSFVXIKANRRPAX

DNA: TTGGCCNCCCGCGGTGGCGGCCGCAAAATTNTATTTNCAAGGGAGACAGTC
 -1: L  A  X  R  G  G  G  R  K  I  X  F  X  R  E  T  V

DNA: ATAATGAAATACCTTTTNGCCTACGGGCCAGCCGCTGGATTGTTATTACTC
 -1: I  M  K  Y  L  X  A  Y  G  P  A  A  G  L  L  L  L
     pComb3 vector                   XhoI    V_Hb primer
DNA: GCTGCCCAACCAGCCATGGCCCAGGTGAAACTGCTCGAGTCAGGACCTGGC
 -1: A  A  Q  P  A  M  A  Q  V  K  L  L  E  S  G  P  G DNA: CTGGTGGCGCCCTCAGAGAGCCTGTCCATCACATGCACTATCTCAGGGTTC
 -1: L  V  A  P  S  E  S  L  S  I  T  C  T  I  S  G  F DNA: TCATTAACCGACGATGGTGTAAGCTGGATTCGGCAGCCTCCAGGAAAGGGT
 -1: S  L  T  D  D  G  V  S  W  I  R  Q  P  P  G  K  G.

DNA: CTGGAGTGGCTGGGAGTAATATGGGGTGGTGGAAGCACATACTTTAATTCA
 -1: L  E  W  L  G  V  I  W  G  G  G  S  T  Y  F  N  S

DNA: CTTTTCAAATCCAGACTGAGCATCACCAGGGACAACTCTAAGAGCCAAGTT
 -1: L  F  K  S  R  L  S  I  T  R  D  N  S  K  S  Q  V

DNA: TTCTTAGAAATGGACAGTCTACAAACTGATGACACAGCCATGTACTACTGC
 -1: F  L  E  M  D  S  L  Q  T  D  D  T  A  M  Y  Y  C

DNA: GCCAAACATGACGGACACGAGACTATGGACTATTGGGGTCAAGGAACCTCA
 -1: A  K  H  D  G  H  E  T  M  D  Y  W  G  Q  G  T  S

DNA: GTCACCGTCTCCTCATCCAAAACGACACCCCCATCTGTCTATCCACTGGCC
 -1: V  T  V  S  S  S  K  T  T  P  P  S  V  Y  P  L  A

DNA: CCTGGATCTGCTGCCCAAACTAACTCCATGGTGACCCTGGGATGCCTGGTC
 -1: P  G  S  A  A  Q  T  N  S  M  V  T  L  G  C  L  V

DNA: AAGGGCTATTTCCCTGAGCCAGTGACAGTGACCTGGAACTCTGGATCCCTG
 -1: K  G  Y  F  P  E  P  V  T  V  T  W  N  S  G  S  L

DNA: TCCAGCGGTGTGCACACCTTCCCAGCTGTCCTGCAGTCTGACCTCTACACT
 -1: S  S  G  V  H  T  F  P  A  V  L  Q  S  D  L  Y  T

DNA: CTGAGCAGCTCAGTGACTGTCCCCTCCAGCACCTGGCCCAGCGAGACCGTC
 -1: L  S  S  S  V  T  V  P  S  S  T  W  P  S  E  T  V

DNA: ACCTGCAACGTTGCCCACCCGGCCAGCAGCACCAAGGTGGACAAGAAAATT
 -1: T  C  N  V  A  H  P  A  S  S  T  K  V  D  K  K  I
     C_H1(γ1)Primer       SpeI     His tag      Stop
DNA: GTGCCCAGGGATTGTACTAGTCATCATCATCATCATCATTAAGCTAGCCTA
 -1: V  P  R  D  C  T  S  H  H  H  H  H  H  *  A  S  L DNA: GTGGTGGCGGTGGCTCTCCATTCGTTTGTGANGATAAAGGCCAATCGNAGA
 -1: V  V  A  V  A  L  H  S  F  V  X  I  K  A  N  R  R

DNA: CCTGCNCNA
 -1: P  A  X

Figure 3

*ATNCTTTNTTGTTCCTTTCTATGC*GGCCCAGCCGGCCATGGCCCAGGTCCAGCTG
CAGGAGTCAGGAACTGAAGTGGTAAAGCCTGGGGCTTCAGTGAAGTTGTCCT
GCAAGGCTTCTGGCTACATCTTCACAAGTTATGATATAGACTGGGTGAGGCAG
ACGCCTGAACAGGGACTTGAGTGGATTGGATGGATTTTTCCTGGAGAGGGGA
GTACTGAATACAATGAGAAGTTCAAGGGCAGGGCCACACTGAGTGTAGACAA
GTCCTCCAGCACAGCCTATATGGAGCTCACTAGGCTGACATCTGAGGACTCTG
CTGTCTATTTCTGTGCTAGAGGGGACTACTATAGGCGCTACTTTGACTTGTGGG
GCCAAGGGACCACGGTCACCGTCTCCTCATGTGGAGGCGGTTCAGGCGGAGG
TGGCTCTGGCGGTGGCGGATCTGACATTGAGCTCACCCAGTCTCCAGCAATCA
TGTCTGCATCTCCAGGGGAGAGGGTCACCATGACCTGCAGTGCCAGCTC
AAGTATACGTTACATATATTGGTACCAACAGAAGCCTGGATCCTCCCCCA
GACTCCTGATTTATGACACATCCAACGTGGCTCCTGGAGTCCCTTTTCGC
TTCAGTGGCAGTGGGTCTGGGACCTCTTATTCTCTCACAATCAACCGAAT
GGAGGCTGAGGATGCTGCCACTTATTACTGCCAGGAGTGGAGTGGTTAT
CCTCTCACGTTCGGCTCGGGCACCAAGCGGGAAATCAAACGGCGGCCGC
AGGTGCGCCGGTGCCGTATCCGGATCCGCTGGAACCGCGT*GCCGCATAGACT-*
*GTTGAA*

B)

MAQVQLQESGTEVVKPGASVKLSCKASGYIFTSYDIDWVRQTPEQGLEWIG
WIFPGEGSTEYNEKFKGRATLSVDKSSSTAYMELTRLTSEDSAVYFCARG
DYYRRYFDLWGQGTTVTVSSGGGGSGGGGSGGGGSDIELTQSPAIMSASP
GERVTMTCSASSSIRYIYWYQQKPGSSPRLLIYDTSNVAPGVPFRFSGSG
SGTSYSLTINRMEAEDAATYYCQEWSGYPLTFGSGTKREIKRAAAGAPVP
YPDPLEPR

Figure 4 tcgctgcccaaccagccATGgcccaggtgaaactgctcgagtcaggacctggcctggtgg
cgccctcagagagcctgtccatcacatgcactatctcagggttctcattaaccgacgatg
gtgtaagctggattcggcagcctccaggaaagggtctggagtggctgggagtaatatggg
gtggtggaagcacatactttaattcacttttcaaatccagactgagcatcaccagggaca
actctaagagccaagttttcttagaaatggacagtctacaaactgatgacacagccatgt
actactgcgccaaacatgacggacacgagactatggactattggggtcaaggaacctcag
tcaccgtctcctcatccaaaacgacaccccatctgtctatccactggcccctggatctg
ctgcccaaactaactccatggtgaccctgggatgcctggtcaagggctatttccctgagc
cagtgacagtgacctggaactctggatccctgtccagcggtgtgcacaccttcccagctg
tcctgcagtctgacctctacactctgagcagctcagtgactgtcccctccagcacctggc
ccagcgagaccgtcacctgcaacgttgcccacccggccagcagcaccaaggtggacaaga
aaattgtgcccagggattgtactagtggtggcggaggtagtggtggcggaggtagcggtg
gcggaggttctggtggcggaggttccgaattcctcgaggtgcccatccaaaaagtccaag
atgacaccaaaaccctcatcaagacaattgtcaccaggatcaatgacatttcacacacgc
agtcagtctcctccaaacagaaagtcaccggtttggacttcattcctgggctccacccca
tcctgaccttatccaagatggaccagacactggcagtctaccaacagatcctcaccagta
tgccttccagaaacgtgatccaaatatccaacgacctggagaacctccgggatcttcttc
acgtgctggccttctctaagagctgccacttgccctgggccagtggcctggagaccttgg
acagcctggggggtgtcctggaagcttcaggctactccacagaggtggtggccctgagca
ggctgcaggggtctctgcaggacatgctgtggcagctggacctcagccctgggtgcacta
gtcatcatcatcatcatcatTAAgctagcctagtggtggcggtggctctcca Maqvkllesgpglvapseslsitctisgfsltddgvswirqppgkglewlgviwgggsty
fnslfksrlsitrdnsksqvflemdslqtddtamyycakhdghetmdywgqgtsvtvsss
kttppsvyplapgsaaqtnsmvtlgclvkgyfpepvtvtwnsgslssgvhtfpavlqsdl
ytlsssvtvpsstwpsetvtcnvahpasstkvdkkivprdctsggggsggggsggggsgg
ggseflevpiqkvqddtktliktivtrindishtqsvsskqkvtgldfipglhpiltlsk
mdgtlavyqqiltsmpsrnviqisndlenlrdllhvlafskschlpwasgletldslggv
leasgystevvalsrlqgslqdmlwqldlspgctshhhhhh

Figure 5 p-ERK 1/2 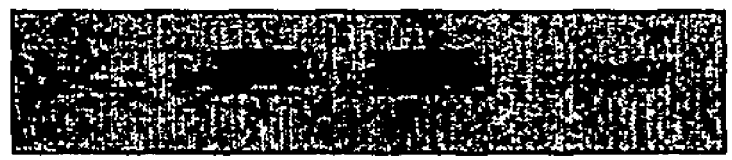
ERK 1/2 
Medium   2C11   2C11   2C11
+ +
Lep  anti-ObR
Figure 15

A)
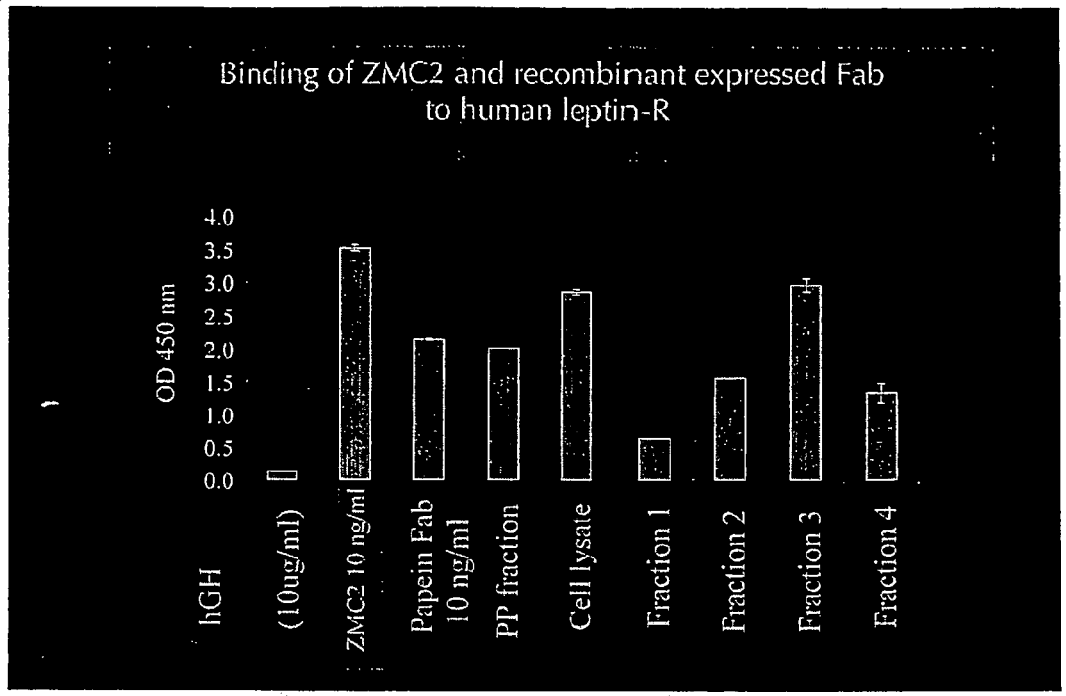
B)
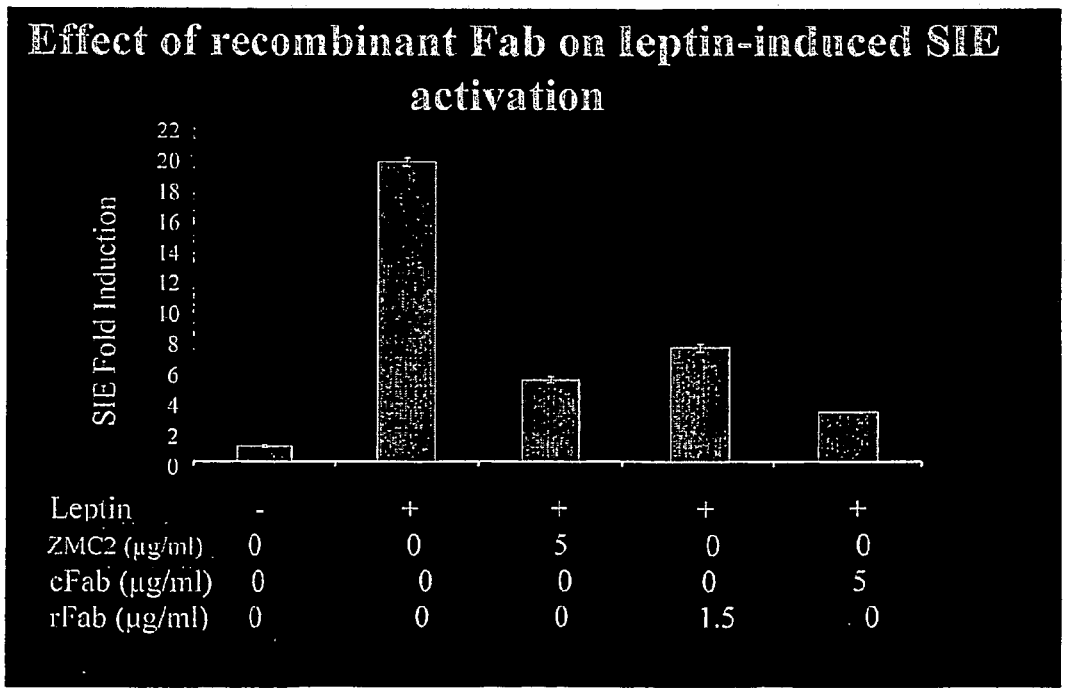
Figure 20

LEPTIN ANTAGONIST AND METHOD FOR QUANTITATIVE MEASUREMENT OF LEPTIN

This invention relates to specific antibodies or fusion proteins, in particular a specific antibody A or a fusion protein directed to a leptin receptor (leptin-R) or a leptin-binding protein (leptin-BP), as well as to the use of these antibodies or fusion proteins for quantitative analysis, for therapeutic purposes and for the preparation of therapeutic drugs. Furthermore, the invention relates to a method for quantitative determination of leptin in the sample of solubilized or suspended leptin-binding proteins by using specific antibodies or fusion proteins according to the invention, as well as to diagnostic agents and (diagnostic) kits containing this antibody or fusion protein.

Leptin (derived of the Greek term leptos=thin) is a protein hormone, that is primarily segregated by the fat cells (adipocytes). In 1994, leptin (Zhang et al. (1994) Nature 372, 425) was discovered as genetic product of the obesitas gene (ob gene) with a molecular weight of approx. 16 kDa, formed by 146 amino acids. It plays an important role in energy metabolism (Friedman et al., (1998) Nature 395, 763-770). Apart from its relevance for energy metabolism, its contribution to the modulation of immunocompetent cells (Lord et al., (1998) Nature 394, 6696) or haematopoietic cells (Sierra-Honigmann et al., (1998) Science 281, 1683-1686) has been described in the meantime as well as a permissive function in the induction of puberty (Quinton et al., (1999) J Clin Endocrinol Metab 84(7), 2336-41). Leptin has also been strongly associated with diabetes and chronic heart failure (CHF) (see E. M. El-Bindary and A. Z. Darwish, Volume 7, Nos 4/5, July-September 2001, 697-706).

In mice (ob/ob mouse), the lack of the leptin gene (ob/ob mouse) leads to massive overweight (adipositas). Due to the fact, that administration of leptin to ob/ob mice induces reduced food uptake and finally weight reduction, leptin was attributed some importance as an appetite suppressant. Anyhow, the situation is far more complex.

The effect of leptin is mediated via the leptin receptor (leptin-R) (Tartaglia et al., (1995) Cell 83(7), 1263-71), thus activating intracellular signal cascades. The leptin receptor pertains to the so-called class I of the cytokine receptor superfamily. In many receptors of this family, an extra-cellular portion of the leptin receptors circulates as leptin-binding protein in the blood, and this is also the case for the leptin receptor.

Defects of the leptin receptor were identified as a cause of overweight problems in human beings (Clement et al., (1998) Nature 392, 398-401). Conversely, patients suffering from anorexia nervosa (diminished appetite) seemingly have increased leptin levels in relation to their reduced fat mass. Therefore, determination of leptin concentration in blood or in serum samples is an important diagnostic tool for clarification of the underlying cause of eating disorders or extreme obesity.

As mentioned above, El-Bindary and Darwish (2001) have strongly associated leptin with diabetes and chronic heart failure (CHF). El-Bindary and Darwish (2001) investigated the interaction of TNF-α, leptin levels and insulin in patients suffering from CHF. CHF constitutes a complex syndrome associated with disturbance in several metabolic and endocrine functions. There is accumulated evidence that weight loss and cachexia seen in advanced stages of CHF constitute a poor prognosis in patients suffering therefrom. In particular, an increased plasma leptin level is assumed to be implicated in the wasting associated with late stage heart failure. Additionally, chronic heart failure is characterized by a hyperinsulinemic state (Swan et al., Journal of the American College of Cardiology, 1997, 30:527-32), in which there is striking loss of both muscle and adipose tissue leading to overt cardiac cachexia in these patients (see Cleland and Clark, European heart journal, 1998, 19:1421-2). Recent attention has therefore been focused on cytokine activity in CHF. According to El-Bindary and Darwish (2001), there is a significant elevation of TNF-α in late stage CHF. Apparently, the level of circulating TNF-α is elevated in patients with advanced CHF. Assumably, TNF-α may contribute to the progression of the cardiac decompensation that occurs in advanced cases of CHF. The results also reveal a correlation between TNF-α and plasma leptin concentration. TNF-α may act directly on adipocytes to increase the production of the lipostatic factor leptin, wherein the level of serum leptin appears to be under control of TNF-α. Hence, there is a significant elevation of the insulin level and a correlation with TNF-α in late stage CHF. El-Bindary and Darwish (2001) also found evidence for a positive correlation between plasma leptin and insulin level in late-stage disease. Increased plasma leptin and associated increase in insulin were considered to be another cachexia causing factor. Increase in plasma TNF-α, leptin and insulin levels, and positive correlation between them in late stage heart failure may constitute one of many vicious circles of advanced stage CHF.

Since disorders of energy metabolism, in particular eating disorders, such as anorexia nervosa (diminished appetite), are observed more frequently, the identification of effective leptin-antagonists that may reduce, inhibit or even block the function of leptin, is of major interest and economic significance.

Therefore, it is a first object of the present invention to provide an antagonist of leptin-R and leptin-BP. Such an antagonist may be suitable in the treatment of diseases and/or symptoms associated with excessive leptin levels, such as diabetes, cachexia, obesity, chronic heart failure (CHF), etc., as well in the development and provision of a medicament and/or therapies for such diseases.

By using suitable leptin-antagonists (as mentioned above), regulatory mechanisms and specific effects of leptin are amenable to examination in vitro by selective inhibition of the leptin receptor and/or displacement of leptin from leptin-binding proteins.

In the light of the above, the quantitative determination of leptin in a sample and in particular in physiological body liquids—such as e.g. blood—is a prerequisite for therapeutic treatment and an important diagnostic tool. Many e.g. hormones or other messenger substances (ligands), bind specifically to their membrane receptors, the extracellular domain(s) of which is (are) frequently solubilized or suspended in the liquid. Thereby, a complex composed of ligands to be determined, e.g. leptin (ligand) and the leptin-binding protein, is formed, which influences (reduces) the level of free ligand in the sample. In order to avoid that problem, a labeled ligand is used and added to the sample. Nevertheless, the binding protein may bind to the labeled ligand in the solution and thus, the ligand is not detectable in the sample. Therefore, the binding protein interferes with quantitative ligand measurement and diagnostics.

Generally, so-called immunoassays are used for the analysis of the leptin concentration. They are based on the principle of an interaction of specific antibodies with an analyte. Alternatively, competitive assays are used (such as the radioimmunoassay, RIA), in which labeled leptin competes with the leptin present in the sample for the binding site on an antibody, thus generating a signal being inversely proportional to the concentration of the analyte to be determined. However, nowadays, sandwich-immunoassays are used most frequently, in which an immobilized specific antibody binds the analyte ("capturing antibody"), and subsequently, a second, labeled antibody, directed to a different epitope of the analyte, binds the analyte, which is then immobilized. This generates a signal, that is proportional to the amount of the bound analyte. The best-known example of this measurement method is the "enzyme linked immuno sorbent assay" (ELISA) with a colorimetric endpoint. Other possibilities for the generation of a signal are radioactivity, chemoluminescence or (time resolved) fluorescence.

All assay methods mentioned above are based on the principle of the highly affine, specific binding between an antibody directed to a e.g. hormone ligand—leptin, in this case—and the hormone ligand in the sample to be analyzed.

The main source of interference in the measurement of leptin in serum or blood is the presence of a highly affine leptin-binding protein, namely the soluble extra-cellular portion of the leptin receptor in human serum. The effect of this leptin-binding protein on the measurement result may cause erroneously high or erroneously low values, always depending on the type of assay used (competitive assay or sandwich-assay). In the competitive assay, on the one hand, the labeled leptin (as a so-called "tracer") may be bound by the leptin-binding protein, thus being removed from solution, resulting in erroneously high concentrations. On the other hand, the leptin-binding protein may also block sterically the interaction of the specific antibody with the leptin molecules from a serum sample and thus may also cause erroneously low concentrations in the competitive assay. In contrast, this steric obstruction of the interaction between antibody and hormone generally provokes erroneously low results in the sandwich-immunoassay, since less hormone or less detection antibody will be bound. The error in the measurement results caused by this interference will become particularly relevant in the presence of certain physiological or pathological conditions that are associated with a change of leptin concentration in the blood.

Since Leptin-BP binds leptin in a sample and thus reduces the amount of free leptin in the sample, no unequivocal determination of physiological leptin concentrations can be obtained. Thus, due to the presence of soluble leptin-binding proteins, all experimental data for body fluid leptin levels are biased by interferences between leptin and leptin-binding protein.

In order to develop a standardizable diagnostic method or a therapeutic treatment for diseases such as obesity, diabetes and/or chronic heart failure (CHF), etc., there is a need for selective, specific and effective substances or molecules that bind to a leptin receptor and/or a leptin-binding protein. To date, only few substances or molecules are known, which selectively, specifically and effectively bind to a leptin receptor and/or a leptin-binding protein. Selectivity and specificity are prerequisites for quantitative and qualitative determination. Gonzales et al. (Gonzales et al., (2003) Mol Hum Reprod 9(3), 151-8) for instance report on polyclonal antibodies, that seem to inhibit leptin effects to a certain extent. However, such polyclonal antibodies cannot be reproduced, they cannot be humanized and are available only in limited amounts.

On the one hand, alternative solutions to avoid measurement inaccuracies relate to methodic extraction methods, that are carried out before the actual measurement method itself, in order to eliminate, e.g. the leptin-binding proteins. Anyhow, this implies significantly increased efforts as to the methods used and may simultaneously lead to misleading results. Altogether, to date there is no satisfactory state-of-the-art-solution to the difficulties of eliminating soluble leptin-binding proteins in samples to be analyzed.

Therefore, it is a second object of the invention to provide a method to obtain reliable results of the ligand level, e.g. leptin, of a sample containing leptin-binding protein(s) or leptin receptors with its/their ligand(s).

This object is solved by the present invention, which may render test methods, in particular assays for (body liquid) leptin determination, less susceptible to falsifying interference by leptin-binding protein. Such method may i.a. be suitable for the diagnosis of diseases and/or symptoms associated with excessive leptin levels, such as diabetes, cachexia, obesity, chronic heart failure (CHF), etc.

The inventors of the present invention succeeded in identifying and providing a molecule—in form of an antibody—that in essence specifically prevents the binding of leptin to a leptin receptor (leptin-R) and displaces leptin, which is bound to a leptin-binding protein, from this leptin-binding protein (leptin-BP).

Therefore, the invention provides an antibody A against a leptin receptor (leptin-R) and/or a leptin-binding protein (leptin-BP), characterized in that it fundamentally reduces and, preferably, prevents the interaction of the leptin receptor and/or of the leptin-binding protein with its ligand, i.e. leptin.

A "leptin-binding protein" or "binding protein" (both termed leptin-BP) or "leptin receptor" (leptin-R) within the meaning of this invention comprises all proteins, that can bind with high affinity (specifically) to leptin to be determined in a sample. Leptin-binding protein is usually soluble or be present in the sample as a suspension. Leptin-binding protein is usually found in body liquid samples, e.g. serum, as the extra-cellular portion of the leptin receptor. Anyhow, it may also be located close to the cell membrane. Examples for human sequences of such leptin-binding proteins or binding proteins or leptin receptors are the sequences O95214, P48357 and O15243 (source: Swiss-Prot/TrEMBL). Preferably they are leptin-binding proteins or binding proteins or leptin receptors of human origin, however, this invention also comprises corresponding proteins of all other vertebrates, in particular mammals, such as rat, mouse, pig, horse, cattle. Examples for such sequences are O02671, Q9MYL0, P48356, Q62959, O89013, Q9JLS8 (source: Swiss-Prot/TrEMBL). Preferably, the leptin-binding protein is a physiological leptin-binding protein, solubilized or suspended in liquid, preferably body liquid.

According to the present application, the term "antibody" comprises monoclonal antibodies, polyclonal antibodies, particularly polyclonal monospecific antibodies (i.e. antibodies with different variable regions, which however all recognize a specific epitope), as well as chimeric antibodies, (anti-) anti-idiotypic antibodies (directed to the inventive antibodies), and genetically manipulated antibodies that are all present in bound or soluble form and may—if appropriate—be labeled by "markers" (for example fluorescence marker, gold marker, coupled enzymes). The term "antibody" in the meaning of the present invention typically refers to full-length antibodies of the afore mentioned antibodies. A "full-length" (monoclonal) antibody in the meaning of the present application may be any of the above mentioned inventive antibodies in its full-length form. A full-length antibody of the present invention typically comprises both the domains of the heavy chain and the light chain. The heavy chain of the inventive antibody includes domains $C_H1$, $C_H2$ or $C_H3$ of the constant region and the variable heavy ($V_H$) immunoglobulin domain. The, the light chain of the inventive antibody includes the variable light immunoglobulin domain ($V_L$) and the constant light immunoglobulin domain ($C_L$). Antibodies, not containing all the aforementioned domains or regions of an antibody are fragments of antibodies within the meaning of the present invention. Fragments of antibodies according to the present invention are further defined below.

Apart from the inventive antibodies as such, antibodies according to this invention may also be provided as portion of a fusion protein containing other (protein)-constituents. Fusion proteins containing an inventive antibody or its fragment thereof are defined below. All of the aforementioned embodiments fall under the scope of an inventive antibody A.

Antibodies according to the present invention may pertain to one of the following immune globulin classes: IgG, IgM, IgE, IgA, GILD and, if applicable, a subclass of the aforementioned classes, such as the subclasses of the IgG or their mixtures. IgG and its subclasses such as IgG1, IgG2, IgG2a, IgG2b, IgG3 or IgGM are preferred. The IgG subtypes IgG1/k or IgG2b/k are specifically preferred.

Antibodies in the sense of this invention are furthermore proteins or possibly other structures produced by vertebrates or by artificial production methods, that bind with high affinity to a determined surface conformation (epitope) of an antigen, i.e. of another molecule, preferably mono- or polyclonal (partial) structures of the above mentioned immune globulins or also polyclonal monospecific antibodies. Typically, such antibodies contain at least the variable part of immune globulins, and, as the case may be, at least one domain of the constant domain of immune globulins, too.

"Polyclonal antibodies" in the meaning of the present application are typically heterogeneous mixtures of antibody molecules, produced from animal serums, that had been immunized with an appropriate antigen, i.e. a ligand of the antibody A of the present invention, preferably with leptin-BP and/or leptin-R.

A "monoclonal antibody" contains a fundamentally homogeneous population of antibodies, that are directed specifically to antigens, and fundamentally, antibodies show similar epitope-binding sites here. The different antibody variants with mono-specificity may belong to the immune globulin classes described above. They may also be mixtures of different major primary classes or subclasses, preferentially, they consist of a homogenous mixture of IgG-antibodies. This homogeneity may also be achieved by an additional purification step (immuno-precipitation, chromatography, for example by using antibodies directed to IgG).

Monoclonal antibodies may also be obtained by using methods known in the state-of-the-art (e.g., Köhler und Milstein, Nature, 256, 495-397, (1975); U.S. Pat. No. 4,376,110; Ausübel et al., Harlow und Lane "Antikörper": Laboratory Manual, Cold Spring, Harbor Laboratory (1988); Ausubel et al., (eds), 1998, Current Protocols in Molecular Biology, John Wiley & Sons, New York)). The aforementioned references are included herein in their entirety. "Monoclonal" is intended to mean in particular the product of an artificial construct, in which an antibody-producing cell (B-cell) is fused with an immortalized cancer cell (hybridom), creating a hybridoma cell. Specific antibodies, that are all exclusively directed to one epitope, are produced by this cell. A hybridoma-cell clone, producing monoclonal antibodies according to the present invention, is cultured in vitro.

"Genetically manipulated antibodies" according to the present invention may also be produced using the methods described in the aforementioned publications.

"Chimeric antibodies" according to the present invention are molecules, that contain different constituents, which are derived from different animal species (e.g. antibodies, showing a variable region, that is derived from a monoclonal mouse antibody and a constant region of a human immunoglobulin). Chimeric antibodies are preferably used on the one hand for the reduction of immunogenicity, if administered, and on the other hand for the increase of yield, e.g., murine monoclonal antibodies yield higher rates of production from hybridoma cell lines, however, they are also associated with a higher immunogenicity in humans. Therefore, human/murine chimeric antibodies are preferably used. Chimeric antibodies and methods for their production are known state-of-the-art methods. (Cabilly et al., Proc. Natl. Sci. USA 81: 3273-3277 (1984); Morrison et al. Proc. Natl. Acad. Sci USA 81:6851-6855 (1984); Boulianne et al. Nature 312 643-646 (1984); Cabilly et al., EP-A-125023; Neuberger et al., Nature 314: 268-270 (1985); Taniguchi et al., EP-A-171496; Morrion et al., EP-A-173494; Neuberger et al., WO 86/01533; Kudo et al., EP-A-184187; Sahagan et al., J. Immunol. 137: 1066-1074 (1986); Robinson et al., WO 87/02671; Liu et al., Proc. Natl. Acad. Sci USA 84:3439-3443 (1987); Sun et al., Proc. Natl. Acad. Sci USA 84:214218 (1987); Better et al., Science 240: 1041-1043 (1988) und Harlow und Lane, Antikörper: A Laboratory Manual, as quoted above). These references are also included in the present invention, as if disclosed in their entirety.

An "anti-idiotypic antibody" according to the present invention is an antibody that recognizes a determinant, which is generally associated with the antigen binding site of an antibody according to the present invention, e.g. an anti-leptin-binding protein antibody. An anti-idiotypic antibody can be produced through immunization of an animal of the same species and the same genetic type (e.g. a mice strain) as a point of origin for a monoclonal antibody, against which an anti-idiotypic antibody according to this invention is targeted. The immunized animal will recognize the idiotypic determinants of the immunizing antibody through the production of an antibody, that is directed to the idiotypic determinants (namely against an anti-idiotypic antibody according to the present invention), (U.S. Pat. No. 4,699,880). An anti-idiotypic antibody according to the present invention may also be used as an immunogen, in order to provoke an immune response in another animal and to induce the production of a so-called anti-anti-idiotypic antibody there. The anti-anti-idiotypic antibody may be, but does not have to be, identical to the original monoclonal antibody with reference to the design of its epitope, that had caused the anti-idiotypic reaction. This allows the identification of other clones, that express antibodies of identical specificity, with the use of an antibody directed to idiotypic determinants of a monoclonal antibody.

In order to induce binding of anti-idiotypic antibodies in the respective animals, such as e.g. the BALB/c mouse, monoclonal antibodies, directed to a physiological binding protein of a physiological ligand, e.g. leptin-binding protein, solubilized or suspended in body liquids, can be used. Cells taken from the spleen of such an immunized mouse can be used to produce anti-idiotypic hybridoma-cell lines, that secrete anti-idiotypic monoclonal antibodies. Furthermore, anti-idiotypic monoclonal antibodies may also be coupled to a medium (KLH, "keyhole limpet hemocyanin") and subsequently be used for further immunization of BALB/c-mice. The sera of these mice contain anti-anti-idiotypic antibodies, that exhibit the binding properties of the original monoclonal antibodies and that are specific for a physiologic binding protein solubilized or suspended in body liquids of a physiologic ligand (ref. preferred examples below). Therefore, the anti-idiotypic monoclonal antibodies have their own idiotypic epitopes or "idiotopes", characterized by a similar structure as the structure of the epitope to be examined In a preferred embodiment of the invention, the inventive antibody is directed to the extra-cellular domain of a leptin receptor, in particular to a leptin-binding protein. In a more preferred embodiment, the antibody A according to the present invention is directed to the leptin-binding site on a leptin-binding protein, to which the ligand (e.g. leptin) binds. Furthermore, the ligand is preferably leptin. In this context, the term "antibody directed to the leptin-binding site on a leptin-binding protein", means that the antibody as a binding epitope binds specifically and with high affinity to the binding site of the ligand (e.g. leptin) on the leptin-binding protein.

Furthermore, an antibody of the present invention may also be bispecific, that is to say, it may also recognize different epitopes with its two paratopes, preferably two different epitopes of the same protein or peptide (see above). Eventually, both paratopes may be structural different, however, they may still bind the same epitope or at least overlapping areas of these epitopes.

According to another embodiment, the antibody A according to the present invention is humanized and directed to a human leptin receptor or a human leptin-binding protein. Humanization of antibodies is known in the prior art can be performed by a large variety of standard methods. Therefore, human or humanized antibodies are also understood as antibodies according to the present invention.

"Fragments" of an antibody according to the present application are also encompassed by the present invention. A "fragment of an antibody according to the pre-sent application" typically may comprise any fragment of an antibody of the present application, either fragments of a polyclonal or monoclonal antibody. A fragment of an inventive antibody thus may comprise e.g. the constant regions of the heavy chain of the inventive antibody, e.g. $C_H1$, $C_H2$ or $C_H3$, the variable heavy ($V_H$) immunoglobulin domain, the variable light immunoglobulin domain ($V_L$), or the constant light immunoglobulin domain ($C_L$). The constant heavy immunoglobulin domain is typically an $F_c$ fragment comprising the $C_H3$ domain and/or the $C_H2$ and/or the $C_H1$ domain. The variable light immunoglobulin domain is preferably an $F_{ab}$ fragment comprising the $V_L$ domain. Also encompassed are all shortened or modified antibody fragments presenting one or two binding sites complementary to the antigen, such as antibody parts with a binding site corresponding to the antibody, composed of a light and a heavy chain, such as $F_v$-, $F_{ab}$- or $F_{ab}'$)$_2$-fragments or single-chain antibody fragments (scF$_v$). Shortened double strand fragments, such as $F_v$-, $F_{ab}$- or $F_{ab}'$)$_2$ are preferred. $F_{ab}$ and $F(_{ab}')_2$-fragments have no $F_c$-fragment, which would be present for instance in an intact antibody, therefore, they may be transported faster in the blood circulation and show comparably less non-specific tissue binding than intact antibodies. In this context, it is stressed, that $F_{ab}$ and $F_{ab}')_2$ fragments of antibodies according to the present invention can be used in an inventive method in the sense of the invention presented. Such fragments are typically produced by proteolytic cleavage, using enzymes, such as e.g. papain (for the production of $F_{ab}$-fragments) or pepsin (for the production of $F(_{ab}')_2$, fragments), or by chemical oxidation or by genetic manipulation of the antibody genes.

Furthermore, fragments of the antibodies of the present invention are typically functionally homolog to the antibodies of the present invention.

"Functionally homolog" in the meaning of the present invention means that a fragment, a variant, etc. of an antibody of the present invention preferably recognizes specifically a sequence of a leptin-R or a leptin-BP. More preferably, a functional homolog of an antibody of the present invention recognizes specifically an epitope of a leptin-R or a leptin-BP.

Even more preferably, the functional homolog of an antibody of the present invention recognizes specifically the leptin binding site of leptin-R or leptin-BP. A functional homolog of an antibody of the present invention means that this homolog is capable of displacing Leptin from its binding to leptin-R or leptin-BP.

A "functional homolog" of an antibody of the present invention is also understood to include antibodies with increased or lowered affinity to leptin-R or leptin-BP and/or increased lowered capability of displacing Leptin from its binding to leptin-R or leptin-BP as compared with a full-length antibody of the present invention. Such a high affinity antibody of the present invention preferably comprises or consists of an amino acid sequence, being encoded by SEQ ID NO: 5 or comprises the amino acid sequence SEQ ID NO: 6. Such antibodies with a modulated activity may excite different biological properties. Furthermore, a person skilled in the art may select an antibody with a specific affinity as necessary in the respective case.

In a more preferred embodiment a fragment of an antibody of the present invention comprises or consists of a protein sequence encoded by a nucleic acid sequence selected from SEQ ID NOs: 2, 4, 5, or 7. Alternatively, such a fragment comprises or consists of a protein sequence selected from SEQ ID NOs: 1, 2, 3, 4, 6 or 8.

In a specific embodiment, the antibody A according to the present invention is the antibody ZMC2. ZMC2 is a monoclonal antibody, directed to the binding site of human leptin on the human leptin-binding protein and in the framework of the invention it had been optimized for the solution of this task. The monclonal antibody ZMC2 has been deposited in viable form by the applicant with entry dated Sep. 25, 2003 under deposit number DSM ACC 2618 along with the reference "ZMC2", assigned by the depositor, according to the stipulations of the Budapest Treaty at DSMZ (Deutsche Sammlung für Mikroorganismen und Zellkulturen GmbH) in Braunschweig.

"Variants" of any of the above mentioned inventive antibodies, particularly variants of the inventive antibody ZMC2, are also contemplated by the present invention. A variant of an antibody, particularly a variant of ZMC2, in the meaning of the present invention typically comprises a sequence, wherein at least one, two or more amino acids, preferably 1-5, 1-10, 1-15 or 1-20 amino acids, of the entire amino acid sequence of said antibody are altered, i.e. deleted, substituted or added with respect to the amino acid sequence of the full-length antibody of the present invention, e.g. ZMC2. Variants of antibodies of the present invention, particularly variants of ZMC2, are preferably functionally homolog to the full-length non-altered antibodies of the present invention, particularly to ZMC2.

"Fusion proteins" are also provided by the present invention. A "fusion protein" according to the present invention typically comprises a portion I and a portion II, wherein portion I may be any antibody or antibody fragment according to the pre-sent invention fused to other (protein)-constituents as portion II. Typically, portion I of such a fusion protein represents a full-length antibody. Alternatively, portion I of such a fusion protein may comprise any of the above mentioned fragments of an inventive antibody, preferably $V_H$ or $V_L$. (Protein)-constituents as portion II of a fusion protein of the present invention typically comprise any antibody or antibody fragment according to the present invention, or any peptide or protein, forming interactions with other proteins, e.g. ligands of leptin-R and/or leptin BP, preferably leptin or fragments or variants of leptin. It is preferred to use components as portion II, which specifically recognize cells to be targeted by the inventive fusion protein. Cells to be targeted are typically adipocytes, connective tissue cells and other leptin binding cells. A fragment of a leptin as used in the inventive fusion protein is preferably a shortened leptin molecule, still capable of binding to the leptin binding site of leptin-R or leptin-BP. A variant of a leptin as used in the inventive fusion protein is preferably a full-length leptin molecule, comprising one or more amino acid substitutions, but still being capable of binding to the leptin binding site of leptin-R or leptin-BP. Therefore, the inventive fusion protein is preferably "bispecific", i.e. it is capable of binding two target molecules, whereby portion I is specific for target molecule I and portion II is specific for target molecule II. If the inventive fusion protein comprises e.g. leptin as portion II of the fusion protein, it may act as a so called "super-antagonist". This is due to the fact that leptin binds as a dimer to. Consequently, a fusion protein consisting of an inventive antibody (or a fragment thereof, both acting as an antagonist) as portion I and leptin (or a fragment thereof, or a high affinity leptin molecule) as portion II enable a fusion protein to bind with a higher strength and a better specificity to leptin-R or leptin-BP and to displace leptin from its binding to leptin-R or leptin-BP even more efficiently than an inventive antibody as such.

Inventive antibodies as constituents of fusion proteins (as portion I or II) are typically provided by using the methods of enzymatic cleavage, protein-synthesis or by using those recombinant methods, as known by the expert in biochemistry or molecular biology.

The inventive fusion protein may comprise an inventive antibody (or a fragment thereof, both acting as an antagonist) as portion I and a second antibody as portion II. Alternatively, the inventive fusion protein may comprise an inventive antibody (or a fragment thereof, both acting as an antagonist) as portion I and a scFv-fragment of the inventive antibody as portion II. Such a fusion protein allows to potentially target the antibody to a specific cell type e.g. to obtain bispecific fusion proteins thereby. Preferably, the bispecific fusion protein is directed to a leptin receptor and/or a leptin-binding protein as first specificity and to a cell surface protein as second specificity of portion II. The inventive antibody, such as ZMC2, may be linked to an antibody, such as CD4-$F_{ab}$, directed to e.g. CD4 (or CD1, 2, 3, 4, 5, 6, 7, 8, 9, 10, CD 25, CD44, etc.). E.g. antibodies recognizing cell surface proteins of specific immune cells allow an inventive fusion protein to specifically bind to immune cells. In this case the affinity of both $F_{ab}$'s could be altered to get a preferential effect. For example, a high affinity CD4-$F_{ab}$ as a bispecific antibody could then target CD4 cells.

Portions I and II of the inventive fusion protein optionally may be linked by a linker sequence. Preferably, the linker comprises a length of about 5 to 40 amino acids, more preferably between 5 and 30 amino acids and most preferably between 5 and 20 amino acids. Also preferably, the linker comprises a sequence containing at least 50% glycine residues, preferably at least 60%, more preferably at least 70% and most preferably at least 80%.

In a specifically preferred embodiment, the fusion protein of the present invention comprises or consists of a protein sequence encoded by the nucleic acid sequence SEQ ID NO: 7 or of the protein sequence SEQ ID NO: 8.

Furthermore, an inventive antibody, a fragment thereof or a fusion protein according to the present invention, may have further covalently (or not covalently) coupled molecules or groups, for example a fluorescence marker or other markers, for example a gold label, or specific epitopes, that can be recognized by third molecules.

The subject matter of the invention disclosed herein are also mixtures (compositions) of the inventive antibodies in the above sense, for instance mixtures of monoclonal antibodies or mixtures of monoclonal antibodies with antibody fragments, mixtures of anti-idiotypic antibodies etc.

Another embodiment of the present invention is a method for preferably quantitatively determining a ligand in a sample containing the ligand of a binding protein, e.g. in solubilized or suspended form, wherein at least one antibody A or an inventive fusion protein according to the present invention is added to the sample to be determined (step a). This inventive method (step a) may be followed by a second step (step b) determining the ligand concentration in the sample.

An "antibody A" as used for the present inventive method is defined as given above.

According to the present inventive method, the antibody A or an inventive fusion protein may be added to the sample before or during, preferably before, quantitative determination of the ligand concentration, e.g. leptin, in the sample, and/or may be incubated together with the sample.

An antibody A according to the present invention, that binds exactly and with high affinity to the site of the leptin-binding proteins, to which the ligand binds, is especially preferred. Due to the binding of the inventive molecule, e.g. an antibody A or an inventive fusion protein, a displacement of the ligand (leptin) from the leptin-binding protein occurs, preventing simultaneously binding of the ligand. This displacement will obviously be dependent on the increase of the amount of antibody A or inventive fusion protein added. Thus, a major excess of antibody A or inventive fusion protein over the molar leptin-binding protein concentration is mostly favourable for carrying out the inventive method.

The ligand (e.g. leptin) is "released" through the displacement and can subsequently be measured quantitatively without steric inhibition due to the binding activity of the leptin-binding protein.

A "ligand" as used in an inventive method typically comprises all compounds, that bind with high affinity to a leptin receptor and/or a leptin-binding protein and allow a measurement of their concentration in specific assays, and all compounds that are also determined, for instance for medical purposes. E.g. messenger substances, such as hormones, transmitters, for instance neurotransmitters, extra-cellular signal peptides or proteins, cytokines, chemokines, lymphokines etc. are compounds in the meaning of the present invention. Leptin is a preferable ligand of the invention. A ligand in the meaning o the present invention may also be a "physiological ligand". Such a "physiological ligand" is typically a ligand in the above sense, which is found in the body of a vertebrate, in particular in a body liquid, without being added exogenously. Correspondingly, this is also applicable for the physiological leptin-binding protein, where this is also the leptin-binding protein of the physiological ligand, naturally to be found under physiological conditions.

A "sample" in the sense of this invention is typically to be understood as any type of solution to be tested, in particular solutions of medically relevant substances, such as e.g. blood, lymph, serum, urine, liquor, also in a processed form, prepared for the sample handling. Likewise, it is preferable, if the sample to be determined in the inventive method contains liquid, preferably body liquid, more preferably human body liquid, in particular blood or human blood.

A "body liquid" is to be understood as each liquid obtained from the body of a vertebrate, in particular a mammal, in particular of a human being. In the case of human beings, this would for instance be blood, urine or lymph, but also cytosolic preparations from human cells.

The term "in solubilized or suspended form" in the meaning of the present invention is to be understood as any form of solution of the leptin-binding proteins or of the ligand in the broader sense in the solution medium. This also includes situations, in which for instance the leptin-binding protein is about to precipitate or has already precipitated, as long as it is still a constituent of the solution.

"Quantitative determination" in the context of the inventive method is to be understood as any method known by a skilled person for determining the amount of an analyte solved in a sample. This includes explicitly, e.g. quantification by using chromatographic methods with a concurrent standard, in particular a quantification by using the highly affine interaction between antibody and ligand (antigen) via competitive assays or binding assays, such as e.g. a sandwich assay, also in the ELISA format. A specific advantage of this invention is the fact that adding a specific antagonistic antibody or an inventive fusion protein to a sample as disclosed herein can be combined with practically all known—in particular commercially available—test kits or test systems for quantitative analysis of the respective analyte (ligand) without any efforts.

In the inventive method preferably the antibody A or an inventive fusion protein is added prior to or during, preferably prior to the quantitative determination and/or is incubated with the sample.

The sample to be tested is typically incubated together with antibody A or an inventive fusion protein. The term "incubation", as used herein is to be understood as a reaction condition, in which the reaction partners, in other words antibody A or an inventive fusion protein and leptin-binding protein are allowed to react with each other. Typically, antibody A or an inventive fusion protein is added to a sample containing leptin binding protein and leptin. The incubation is generally carried out for a limited period of time, in this case for example 6, 12, 18 or 24 hours. The term incubation has to be understood primarily as prior step—for example for a period of 6, 12, 18 or 24 hours—before the start of the quantitative measurement (for instance with a commercially available test kit) using antibody B for ligand (leptin) detection.

In another preferred embodiment of the method according to the present invention, the leptin-binding protein is a physiological partner of the ligand.

The method according to the present invention is also useful, when the ligand and/or the leptin-binding protein has been added externally (exogenously), e.g. following an injection or other uptake of, for instance, leptin as a ligand in patients or test persons.

The present inventive method can be used to measure any ligand of "binding proteins". Binding proteins are proteins interacting with other proteins. An example of a binding protein is leptin-binding protein or the leptin-receptor, interacting with leptin. The binding protein, as used in a method according to the present invention, is preferably soluble, more preferably a soluble (leptin-)receptor.

In a preferred embodiment of the method according to the present invention, the ligand as bound by a "binding protein" is a peptidic compound and/or a hormone, preferably a peptidic hormone, in particular leptin, or a hormone-binding protein. The term "peptidic" is to be understood here to comprise any compound, of which constituents are predominantly linked together by a peptidic bond (such as R1-NH—C(O)-R2).

Hormone binding proteins, if used as ligands in the inventive method, are preferably binding proteins (see below), that bind affine hormones. A "hormone" herein is to be understood as a chemical messenger substance, that acts at a distance from its site of synthesis and liberation. Hormones are preferably produced by endocrinal glands, for instance the hypophysis, gonads or epiphysis. Examples are the growth hormone or the luteinizing hormone LTH, insulin, melatonin, glucagon, gastrin, angiotensin, substance P, interleukines, vasopressin, endorphines, enkephalines, relaxin, the atrionatriuretic factor or also leptin.

In a specifically preferred embodiment of the method according to the present invention, the ligand used in such a method is human leptin and the leptin-binding protein is human leptin-binding protein. Furthermore, the antibody A or an inventive fusion protein is preferably directed to the binding site of leptin on the leptin-binding protein.

Moreover, it is preferred to add a further antibody B, preferably a monoclonal antibody B, if a ligand of the binding protein according to the inventive method is quantitatively determined. Such an "antibody B", preferably a "monoclonal antibody B", is typically an anti-ligand-antibody, i.e. an antibody, which is directed to any ligand according to the present invention but not to leptin-R or leptin-BP. It is advantageous, if quantitative determination in the inventive method is carried out by using a competitive binding test, preferably a "radio-immuno assay" (RIA). Likewise it is typically favourable to quantitatively determine the ligand concentration by reading out a signal, which depends on the concentration of the ligand to be determined, preferably by using an enzyme-linked immuno sorbent assay (ELISA) and/or an according sandwich-assay.

In another preferred embodiment of the method according to the present invention, no separation of the leptin-binding proteins from the sample to be determined is effected prior to quantitative determination. In particular, this means, that it is not required for the invention disclosed to extract the leptin-binding protein from the sample prior to its quantitative analysis, in contrast to the state-of-the-art methods for the determination of ligand concentrations. In the art, practically each form of extraction is carried out, in which the ligand to be determined—such as for instance the hormone—remains in the sample, while the binding protein is separated from the sample, e.g. by precipitation and/or filtration with determined molecule weight exclusion limits, chromatographic methods, such as e.g. affinity chromatography or HPLC, dialysis in determined ligand sizes etc. Precisely this step can be avoided, preferably while using the method according to the present invention. Due to the selection of antibody A or an inventive fusion protein, neither antibody A/the inventive fusion protein nor the complex formed of antibody A/the inventive fusion protein and leptin-binding protein is able to bind to the ligand to be determined. Therefore, in the sample determination is no longer interfered or falsified by ligand/binding protein interaction, even if the complexed leptin-binding protein remains in the sample. However, use of the highly affine antibodies B for quantitative measurement does not interfere, since they do not bind to antibody A/the inventive fusion protein, to the leptin-binding protein or the complex formed by both, but exclusively to the ligand itself.

This advantage is in particular observed in an especially favourable and preferential method according to the present invention, in which the antibody A/the inventive fusion protein is added in such a way, that subsequent to addition the molar concentration of antibody A is equal or preferably higher than the molar concentration of the leptin-binding protein, preferably at least 50% higher, more preferably at least twice as high, more preferably at least three times as high and in particular at least four times as high as the leptin-binding protein concentration.

Precisely, this addition of the antibody A/the inventive fusion protein in excessive amounts to the leptin-binding protein is especially favourable, since in the presence of a sufficient excess of antibody A/the inventive fusion protein all ligands are displaced entirely from the leptin-binding protein and therefore become measurable. Since the leptin-binding protein is quantitatively complexed, it does not interfere any more with ligand concentration.

The correct and sufficient amount of specific antibody A or of inventive fusion protein to be added to the sample in order to provide a quantitative measurement of the ligand without interference phenomena, can be determined by the expert by simple preliminary tests. The optimal addition depends on the amount of a leptin-binding protein in the sample and eventually on the quantitative test system used or the amount of ligand to be determined.

In a preferred embodiment of the present invention a ligand is quantitatively determined by using antibody B, directed to the ligand, preferably a monoclonal antibody B, in a sample containing human blood. Therein, the ligand and a leptin-binding protein are preferably contained in solubilized or suspended form, and antibody A/an inventive fusion protein is directed to the binding site of the ligand on the leptin-binding protein. Preferably the deposited monoclonal antibody ZMC2, is added as antibody A to the sample to be determined in significant excessive amounts as compared to the amount of leptin-binding protein, before or during quantitative determination of the ligand, preferably before step b (quantitative determination, by adding and incubating antibody B).

Preferably, the ligand as used in a method according to the present invention is leptin.

The present inventive method typically prevents interference of the leptin-binding protein with leptin by adding highly excessive amounts of a specific, preferably monoclonal antibody A, or an inventive fusion protein to the sample to be determined. Antibody A or an inventive fusion protein are directed to the leptin-binding protein. An antibody A as used in the inventive method is preferably the monoclonal antibody ZMC2. It has been selected due to its particularly preferred property to bind to the leptin-binding protein-molecule exactly at the same binding site as the leptin molecule does. If excessive amounts of antibody A are added, it leads to a displacement of the leptin molecules from their binding to the leptin-binding protein. Leptin is "released" and may then be measured by any immunoassay for leptin without sterically induced blocking by leptin-binding protein. Since the "anti-leptin-binding protein-antibody" (antibody A) itself or the inventive fusion protein itself do not interfere with the "anti-leptin antibodies" (antibody B) used for the measurement of leptin (ligand), removal of the complexes consisting of antibody A/inventive fusion protein and leptin-binding protein from the sample is irrelevant. Practically, e.g. special anti-leptin-binding protein antibody ZMC2 with its leptin-displacing property or an inventive fusion protein is added to the sample before the analysis. After incubation with ZMC2 ligand determination follows the respective manufacturer's guidelines.

Another embodiment of the invention relates to a medicament or a vaccine containing at least one inventive antibody A and/or at least one inventive fusion protein. Preferably, a medicament or a vaccine is disclosed, which contains at least one antibody A or an inventive fusion protein according to the present invention and optionally additives and/or adjuvants. Eventually, further active substances may be present in the medicament or vaccine according to present invention.

The medicament or vaccine containing at least one antibody A and/or an inventive fusion protein according to the present invention is suitable, for instance for the treatment of excessive leptin levels. The inventive antibody may inhibit—preferably entirely—all leptin receptor binding sites. As a consequence, leptin cannot bind to its leptin receptor and/or the therapeutic antibody A/the inventive fusion protein displaces leptin, which is bound to a leptin-binding protein, from its binding site.

According to a further embodiment, an antibody A/the inventive fusion protein according to the present invention or a medicament or vaccine containing at least one inventive antibody A/the inventive fusion protein may be used therapeutically as a leptin-antagonist or may be used for the preparation of a medicament, that inhibits the physiological effect of human leptin. The physiologic effect is blocked by an antibody A/the inventive fusion protein according to the present invention due to its binding to the leptin binding site of the leptin-binding receptor.

A medicament or vaccine, containing one or more antibodies A according to the present invention (and, if applicable, further adjuvants or additives) and/or an inventive fusion protein, can therefore be used for therapeutic purposes also in any of those diseases, disorders or conditions showing unphysiologically increased leptin levels. This also implies, according to the present invention, the use of such inventive antibodies A/fusion proteins, medicaments or vaccines containing at least one antibody A for the treatment (or for the preparation of a medicament for the treatment) of all those disorders, diseases or pathophysiologies, for which excessive leptin levels are etiological, for example diseases of the energy metabolism, pathologic eating disorders, such as anorexia or cachexia. The inventive antibodies A or an inventive fusion protein, medicaments or vaccines, containing an antibody A, may also be used in the treatment of TH1 mediated diseases including multiple sclerosis, diabetes, type 1 diabetes, chronic heart failure (CHF), TNF-mediated diseases, autoimmune colitis, rheumatoid arthritis, systemic lupus erythematosus, and transplant rejection, for the regulation of increased proliferation of naturally occurring regulatory/suppressor T cells and treatment of diseases associated therewith, and diseases associated with the MAPK/ERK1-2, AKT, p-27-kip1 signalling pathways.

Moreover, there are experimental results that document a correlation of leptin values and autoimmune disorder disposition.

The inventive antibodies A, medicaments or vaccines, containing an antibody A or an inventive fusion protein, may also be used to block immune effects of leptin. The inventive antibodies A, fusion proteins, medicaments or vaccines, containing an antibody A or a fusion protein, therefore may be used for immune therapy.

By administration of at least one antibody A according to the present invention, or an inventive fusion protein or the respective inventive medicaments or vaccines, the effects of pathophysiologically increased extra-cellular leptin-concentration can be blocked without decreasing its serum concentration. Therefore, it is highly useful and promising, to use the inventive medicament or vaccine also for the treatment of diseases such as anorexia nervosa and in the different stages of cachexia. The hypersecretion of leptin in the case of insulin-dependent diabetes mellitus, which is made responsible for a variety of sequelae, may also be treated by an leptin-antagonist according to the present invention or a medicament or vaccine containing at least one antibody A.

Where appropriate, a therapeutic treatment of affected patients with excessive leptin levels may carried out in combination with such medicaments or active substances, that decrease the secretion of leptin.

A medicament or a vaccine according to the present invention, an inventive antibody A or an inventive fusion protein is particularly preferred or may serve for the preparation of a medicament, for the treatment of conditions, that are associated with an undesired activation of the immune system as well as with autoimmune diseases. Autoimmune diseases may be selected e.g. from multiple sclerosis (MS), rheumatoide arthritis, diabetes, diabetes type I, systemic lupus erythematosus (SLE), chronic polyarthritis, Basedow's disease, autoimmune forms of chronic hepatitis, colitis ulcerosa, allergie type I-diseases, allergie type II-diseases, allergie type III-diseases, allergie type IV-diseases, fibromyalgie, alopecia, Morbus Bechterew, Morbus Crohn, Myasthenia gravis, neurodermitis, polymyalgia rheumatica, progressive systemic sclerosis (PSS), psoriasis, Reiter-syndrome, rheumatic arthritis, vaskulitis, etc.

In a specific embodiment, a medicament according to the present invention, an inventive antibody A or an inventive fusion protein may be used or may serve for blocking peripheral effects of leptin. "Peripheral" effects are evoked by inhibiting leptin effects indirectly via blocking the leptin receptor. In contast, "central" inhibition of leptin are due to direct interaction of a therapeutic compound with leptin.

Leptin acts peripherically e.g. on the immune system, whereas central effects are based on its binding to central control organs, e.g. the hypothalamus. Leptin's binding to the hypothalamus leeds to weight control effects. For the treatment of certain immune disorders the interaction of leptin with its receptor shall be inhibited, whereas the leptin level in the other body parts (e.g. hypothalamus) shall remain unchanged in order to avoid considered weight loss/weight gain.

State-of-the-art treatment of leptin excess e.g. by administering anti-leptin-antibodies, lowers the leptin level in the body. Upon administration if anti-leptin-antibodies positive effects on the patient's immune disorder may be achieved. However, simultaneous side effects may appear, such as weight gain due to decreased levels of free leptin, e.g. at the hypothalamus. The inventive antagonist allows to avoid the side effects induced by state-of-the art anti-leptin-antibodies. The anti-leptin-receptor antibody therapy according to the present invention as disclosed herein does not reduce the patient's leptin level by selectively blocking the leptin receptors of certain tissues without modifying the leptin responsiveness of other tissues ("central" effect in the hypothalamus). By way of example, while using an inventive antibody A, such as ZMC2, one might prevent an immune response without having an effect on weight, i.e. there is no significant change in weight during treatment with the inventive antibody A, e.g. ZMC2, or the inventive fusion protein.

Typically, an inventive antibody A or an inventive fusion protein as used in a medicament or a vaccine according to the present invention will be available as lyophilized powder, containing between 0.5 mg and 100 mg of the inventive antibody A, and further additives, as for example glycin, manitol, and/or sodium phosphate monohydrate. This lyophilized powder is provided in a suitable aqueous solution and administered subsequently, for example subcutaneously once or several times per day.

In principle, the medicaments according to the present invention may also be administered as liquid dosage form, in particular in form of injection solutions. Suitable additives and/or adjuvants are e.g. solutions or diluents, stabilizers, suspension mediators, buffer substances, preservatives, as well as colorants, expanders, and/or binders. The selection of the adjuvants as well as of the amounts to be administered depends on whether the medicament shall be administered parenterally, intranasally, intravenously, intraperitoneal or intramuscular. Preparations in form of suspensions and solutions as well as dry preparations, which allow an easy reconstitution, are suitable for all the parenteral applications.

Another embodiment of the invention is a diagnostic agent containing at least one antibody or fusion protein according to the present invention as well as, where appropriate, additives and/or adjuvants. A "diagnostic agent" is to be understood as a preparation or an adjuvant which may be useful, for example for the diagnosis of a determined disease.

A further embodiment of the invention is a kit containing distinct from each other at least one first preparation containing at least one antibody A or fusion protein according to the present invention and one operating test assay ready for use, based on an antigen/antibody-reaction, for the quantitative determination of a ligand, that serves as an antigen in this test.

A kit is to be understood as a conjunct form of different constituents in a packaging form. In this case it is in particular a diagnostic-kit, that contains the different constituents required for the quantitative analysis of a ligand.

A kit is preferred, in which the first preparation contains an antibody A or fusion protein, directed to the binding site of the ligand, preferably leptin, especially preferentially human leptin, on the preferably human, leptin-binding protein, and/or which contains, apart from the first preparation and the operative test assay ready for use, based on an antigen/antibody-reaction, for the quantitative determination of a ligand, also a preparation for the calibration.

An especially preferable embodiment is a kit according to the present invention, in which the first preparation contains the antibody ZMC2 (deposited, see above) and/or the preparation for the calibration and/or the antibody B in the enclosed operating test assay ready for use, wherein the test assay is based on an antigen/antibody-reaction for quantitative determination of a ligand, wherein antibody B, preferably a monoclonal antibody B, is directed to the ligand.

Preferably, the ligand is leptin and the antibody B is directed to the main isoform of leptin with a molecular weight of 16 kDa.

A further embodiment of the invention is the use of at least one antibody for determination, preferably quantitative determination, of a physiological ligand, preferably leptin, of a physiological leptin-binding protein.

A further subject matter of the invention is a method for preparing an antibody according to the present invention, i.e. an antibody directed to a leptin-binding protein, which is further directed to a ligand, comprising the following steps: (a) immunization of animals with recombinantly produced leptin-binding protein, (b) isolation of immune cells from the animal, (c) fusion with myeloma-cell lines to hybridoma cell cultures, (d) selection of clones with high specificity for the leptin-binding protein. The immunization can carried out with all animals suitable for such purposes, such as mice, rabbits, pigs, horses etc. In order to separate such clones, that produce antibodies directed to a leptin-binding protein, from inventive clones (that produce antibodies, which are e.g. specifically directed to the ligand binding site of the leptin-binding protein), suitable media (e.g. wells of microtiter plates, polystyrol beads, plastic tubes) are each coated with one (unselected) anti-leptin-capture antibody in a method step (e). In another method (f), the leptin-binding protein and subsequently the ligand (e.g. leptin) are added. Thereby, the ligand should is preferably labeled (for example by using biotinylation, label (radioactive label, fluorescence marker, enzyme marker (horseradish-peroxidase) etc.)) or be detectable by using a respective anti-ligand-antibody, such that the property of the ligand, to bind to the leptin-binding protein in the recipient coated with capture antibody can be examined. Thus, alternative methods are for instance radioactivity, chemoluminescence, colorimetric methods or an enzyme reaction. After the washing step, those "wells" or "beads" that do not show a signal after the addition of the ligand, can be identified. In this case, the capture antibody blocks the ligand binding site. Thus, the binding site is not available any more for the binding of the ligand, since the capture antibody interferes with the ligand.

Finally, an antibody A or a fusion protein according to the present invention can be identified with by carrying out competitive binding assays. As described above, a coating process is required here, though, in this method each well (e.g. of a microtiter plate) is coated with an anti-leptin-binding protein-antibody, that does not specifically recognize the ligand binding site. After addition of the leptin-binding protein, a potentially interesting antibody or a fusion protein (each with the property of specifically recognizing the ligand binding site) is added to each well above with labeled ligand. As the concentration of the antibody specific for the ligand binding site increases, the signal intensity of the ligand in the well decreases. This method may be used for selection of inventive antibodies directed to a leptin receptor and/or a leptin-binding protein.

As an alternative to using hybridoma cells, so-called "phage display" methods (Morphosys or Cambridge Antibody Technologies) may be used, in order to generate potentially inventive antibodies and to select them, as described above.

In the following section, the invention is described in a more detailed way by examples, without limiting the scope of the present invention to these Examples.

EXAMPLES AND FIGURES

Description of Figures

FIG. 2A: shows the protein sequence of the ZMC2/$F_{ab}$ light chain (amended) (SEQ ID NO: 1).

FIG. 2B: depicts the nucleotide sequence of the open reading frame of the pComb3/ZMC2,$F_{ab}$ vector (light chain) (SEQ ID NO: 2) and its translation into the encoding protein sequence of ZMC2/$F_{ab}$ light chain (cf. also FIG. 2A) (SEQ ID NOS: 3-5). Start and stop codons are indicated in bold letters, restriction sites are underlined, and primers sequences are double underlined. The sequence of the pComb3/ZMC2,$F_{ab}$ vector is indicated in italic letters.

FIG. 3A: depicts the protein sequence of ZMC2/$F_{ab}$ Heavy chain-His (SEQ ID NO: 6).

FIG. 3B: shows the nucleotide sequence of the open reading frame of the pComb3/ZMC2,$F_{ab}$-His vector (SEQ ID NO: 7) (heavy chain) and its translation into the encoding protein sequence (SEQ ID NOS: 8-9) of the heavy chain of ZMC2/$F_{ab}$ Heavy chain-His (cf FIG. 3A). Start and stop codons are indicated in bold letters, Restriction sites are underlined, and primers sequences are double underlined. The sequence of pComb3/ZMC2,$F_{ab}$-His vector is indicated in italic letters. The His-tag is indicated by a dotted (.......) line.

FIG. 4A: discloses the nucleotide sequence of the high affinity clone ZMC2 ScFv (1C3) SEQ ID NO: 10). The $V_L$ sequence is indicated in bold letters. The $V_H$ sequence is double underlined. The linker in between is indicated in normal letters. The sequence of the vector is indicated in italic letters. The E-tag is indicated by a dotted line. Restriction sites (SfiI and NotI) are underlined, and primers sequences are double underlined.

FIG. 4B: shows the translated protein sequence (SEQ ID NO: 11) encoded by the nucleotide sequence of the high affinity clone ZMC2 ScFv (1C3) as shown in FIG. 4A. Disclosed is the sequence from $V_H$ until the end of the E-tag.

FIG. 5A: depicts the nucleotide sequence of the ZMC2 Heavy chain —Leptin construct (SEQ ID NO: 12). Disclosed is the 1203 by nucleotide sequence, wherein start and stop codons are indicated in bold letters and restriction sites are underlined. The ZMC2 heavy chain is indicated by a dotted (.........) line, the $(G_4S)_4$ linker is double underlined. The sequence of Leptin indicated by a (_____) line and is the vector is indicated in italic letters. The his tag is indicated by a (_____) line.

FIG. 5B: shows the translated protein sequence of the ZMC2 Heavy chain —Leptin construct (SEQ ID NO: 13) (cf. FIG. 5A). The ZMC2 heavy chain is indicated by a dotted (..........) line, the $(G_4S)_4$ linker is double underlined. The sequence of Leptin indicated by a single line and is the vector is indicated in italic letters. The his tag is indicated by a (_____) line.

FIG. 6 clearly shows that ZMC2 antibody binds to human leptin-R in a dose dependent manner (cf. Example 3).

In FIG. 12A ZMC2 is shown (from 001, 0,1, 1 and 10 ug/ml) in the presence or absence of exogenous leptin (100 ng/ml). As may be obtained from FIG. 12A, there is a minor effect of ZMC2 to increase PBL proliferation that is reduced by leptin (cf. Example 9).

FIG. 13 shows the stimulation by okt3 (optimal dose 100 ng/ml) of human PBL in autologous human serum with different doses of leptin and more points on ZMC2 mAb dose response (0, 0.005, 0.05, 0.5, 5, 50 ug/ml) are shown. ZMC2 antibody stimulates proliferation, which is then clearly reversed by addition of leptin. Thus, ZMC2 clearly reacts as an antagonist to leptin-R regarding the overall response on the mixed T-cell population (cf. Example 10).

In FIG. 14A, percent in body weight change is flat during treatment with leptin alone, and instead of being prevented by ZMC2, the weight was slightly increased in terms of no change or even little reduction in body weight. On the heterozygotes (FIG. 14B, cf. Example 11), treated in parallel, basically show the similar results. With the same dose of ZMC2 alone, the untreated mice slightly increase body weight over the time; In a comparative Experiment (FIG. 14C, cf. Example 9) proliferation of spleen cells from normal mouse (B6) was stimulated with anti-CD3 for mouse (called 2C11) (0,0001, 0,001, 0,01, 0,1, 1, 10, 100 ug/ml) dose response in the presence of FCS 2%. As can be seen in FIG. 14C, a clear inhibition can be obtained at 10-100 ug/ml.

FIG. 15: displays a photograph of a gelelectrophoresis. The samples applied on the gel were obtained from an anti-CD3 stimulation experiment using T-cells from autoimmunity-prone NOD mice. As may be obtained from the gel ERK1/2 phosphorylation is reduced by the leptin-R blocking antibody.

FIG. 20A: shows a bar plot of a binding experiment of ZMC2 and recombinant expressed $F_{ab}$ ZMC2 to human Leptin. The y-axis shows the absorbance at 450 nm (OD 450 nm).

FIG. 20B: shows the effect of recombinant $F_{ab}$ ZMC2 on leptin-induced SIE activation. As can be obtained from FIG. 20A recombinant $F_{ab}$ ZMC2 ($rF_{ab}$) and chemically made $F_{ab}$ ZMC2 ($cF_{ab}$) for ZMC2 block leptin signalling.

EXAMPLES

Example 1

Production of Antibody A

Directed to Leptin-BP

Figure 1:
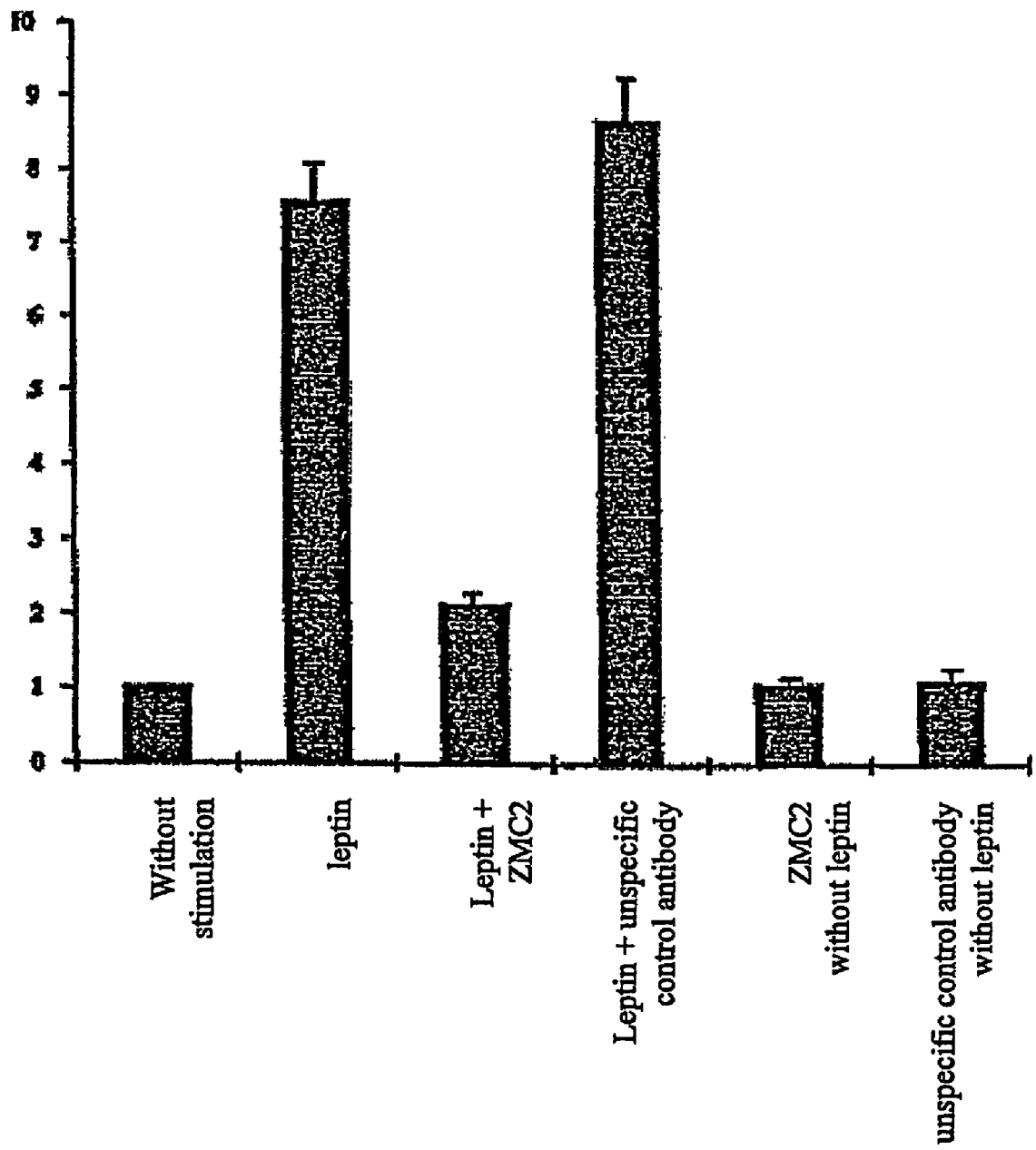
FIG. 1: shows the results of the examination in Example 2. The results prove, that addition of the inventive antibody may diminish or abolish the influence, which leptin mediates via the leptin receptor.

More than 20 Balb/c mice were repeatedly immunized with leptin-BP produced recombinantly according to the generally known method (ref. to leaflet of Titermax®). When a high titer against leptin-BP was achieved, the spleen has been removed from the animals, and according to the method described by Köhler and Milstein (Continuous cultures of fused cells secreting antibody of predefined specificity, Nature, 1975, Aug. 7; 256 (5517): 495-7) hybridoma cell cultures were produced by fusion with a mouse-myelom-cell line. Also according to generally known methods (limited dilution, screening of the hybridoma cell culture supernatants with labeled antigen) those clones were selected, which produced monoclonal antibody with high affinity and specificity for leptin-BP.

The majority of the selected clones were directed to such epitopes on the leptin-BP molecule, that are situated externally of the binding site for leptin. In order to select antibodies A according to the present invention, directed to an epitope within the binding site, at first one of many antibodies, that binds leptin-BP externally of the binding site, was used. It was identified by applying all monoclonal antibodies against leptin-BP (as many as possible), e.g. in separate wells each, on a microtiter plate (polystyrol plates with highly adsorptive surface) as capture antibody, (alternatively, other methods, as e.g. coated polystyrol beads, coated plastic tubes etc., may also be used). Subsequently, recombinant leptin-BP has been added, which binds to the coating antibody—in a primarily still unknown arrangement (binding according to each epitope within or externally of the interaction site of the hormone receptor). Finally, labeled (in our case biotinylized) leptin has been added, which may now bind exclusively to the leptin-BP-molecules, and which possess a freely accessible binding site (i.e., where the coating antibody does not interfere with the leptin binding). Determination of bound antibody was carried out by addition of streptavidin-europium, which binds to an bound biotinylized leptin and can be measured in a fluorimeter (time resolved fluorescence after addition of enhancement solution). Alternatively, this step may also be effected using analog methods (radioactivity, enzyme reaction/colorimetric method or chemoluminescence).

In order to find an antibody, that is directed to the binding site, a microtiter plate was coated with an antibody against leptin-BP, selected according to the above method, that does not interfere with the binding of leptin. The addition of leptin-BP provoked an aligned binding of the leptin-BP-molecules, that is to say with a freely accessible binding site for leptin. Subsequently, biotinylized leptin was added and simultaneously, all other monoclonal antibodies against leptin-BP (once again each antibody in an own well of the microtiter plate). If an antibody is then directed to the binding site, it should block the binding of biotinylized leptin in a concentration dependent manner. This could be detected by a decrease of the signal intensity (detection method in our case again time resolved fluorescence (streptavidin-europium). For confirmation in an inverted experiment a displacement of biotinylized antibodies directed to leptin-BP by adding unlabeled leptin was carried out. This is possible, if the biotinylized antibody competes with the non-labeled leptin for the binding on the receptor binding site, i.e. if the epitope of the mAbs is located at the interaction site of the leptin/leptin receptor.

Example 2

Verification of the Effectiveness of an Antibody According to the Present Invention And the Associated Improvement of General Quantitative Measurement Methods in The Presence of Interfering Leptin-Binding Protein Leptin-binding protein was immobilized on a microtiter plate such, that the binding site for leptin was freely accessible. This is carried out by using other antibodies directed to the leptin-binding protein, that do not bind within, but externally at the hormone-receptor-interaction site. Subsequently, labeled (biotinylized) leptin was added. Then, buffer solutions with ascending concentrations of the inventive antibody ZMC2 are added to the incubation solutions. Following an incubation time of 2 hours, the amount of labeled leptin bound to immobilized leptin-binding protein was measured by addition of a fluorescence dye, that binds specifically to biotin. With an ascending concentration of ZMC2, the binding of biotinylized leptin decreased, thus proving the displacement effect of ZMC2.

Furthermore, the functional blockade of the leptin receptors was proven in a cell culture assay by using ZMC2. Therefor, HEK293-cells were transfected transiently with the human leptin receptor as well as with a STAT 3-luciferase-reporter. This construct enables the visualization or the measurement of the intracellular signal cascade activation caused by leptin.

As shown in FIG. 1, the addition of leptin to the cell culture provokes a 7-8-fold increase of the luciferase activity (compared with the control containing no leptin). Adding the inventive antibody ZMC2 to the preparation (5 µg/ml) prevents this activation in contrast to the control antibody (antibody with irrelevant specificity, in this case against KLH).

Example 3

Binding of ZMC2 Antibody to Human Leptin-R on ELISA

Figure 6:
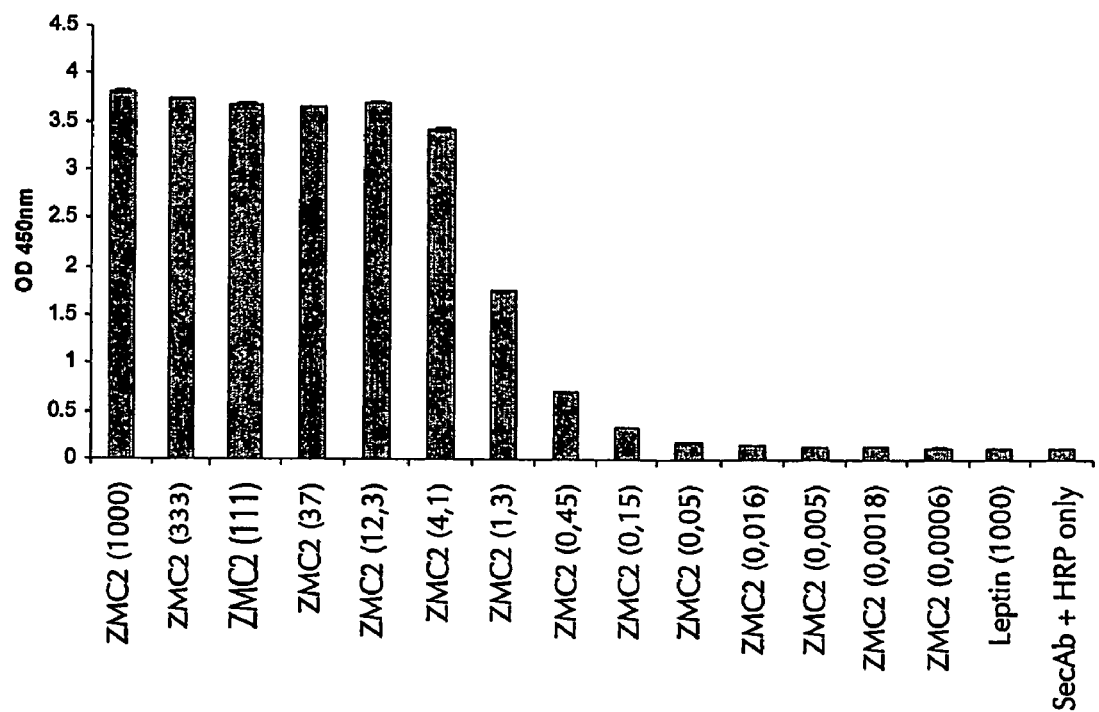
FIG. 6: illustrates the binding of ZMC2 antibody to human leptin-R on ELISA.

For detecting binding of ZMC2 antibody to human leptin-R an ELISA plate was coated with recombinant human leptin-R (200 ng/well) and different concentrations of ZMC2 antibody (1000, 333, 111, 37, 12,3, 4,1, 1,3, 0,45, 0,15, 0,05, 0,016, 0,005, 0,0018, 0,0006 ng/ml) were added. Binding of ZMC2 antibody to leptin-R was detected subsequently using a biotinylated secondary antibody followed by SAV-HRP and the signal (OD of resulted colour) was measured at 450 nm. As a result, ZMC2 antibody binds to human leptin-R in a dose dependent manner as may be obtained from the corresponding bar plot (see FIG. 6).

Example 4

Specificity of Binding of ZMC2 Antibody to Human Leptin-R

Figure 7:
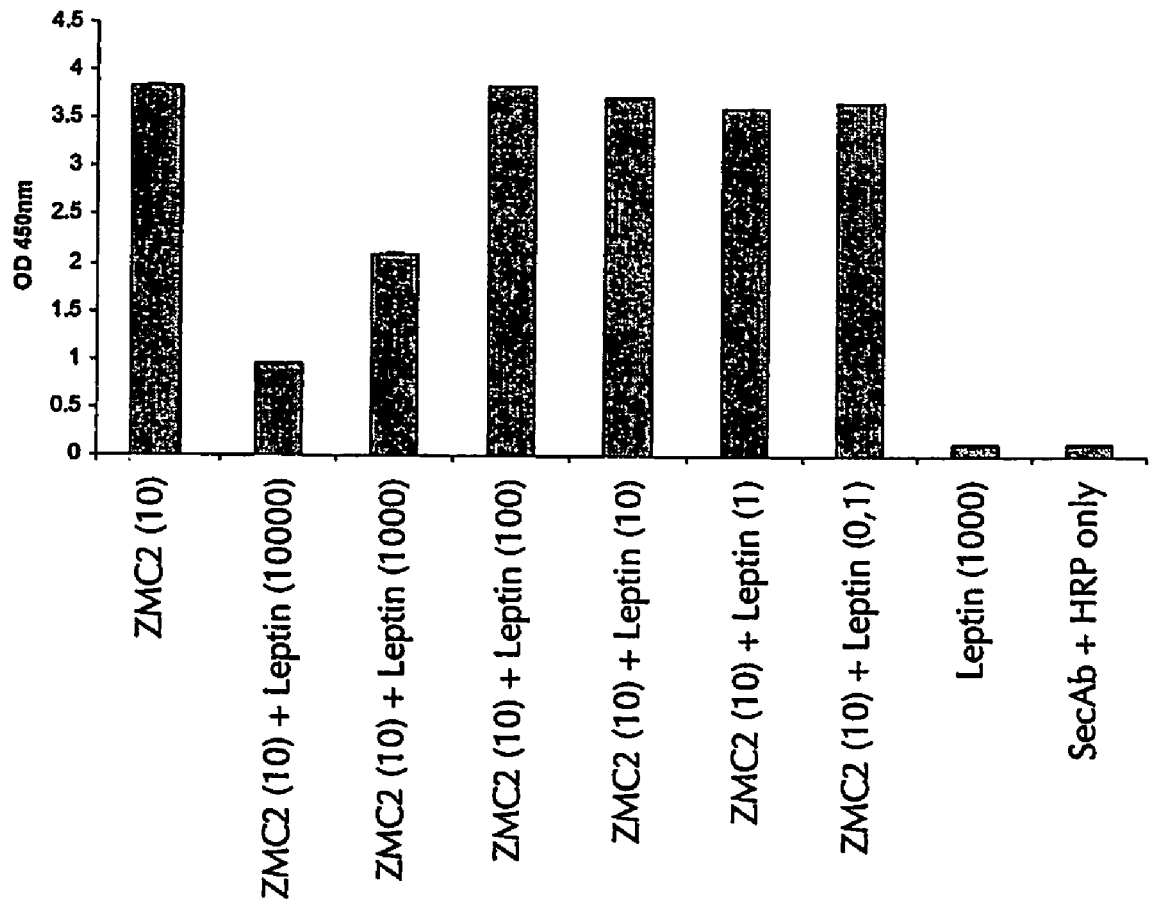
FIG. 7: shows a bar plot indicating the results of a competitive binding experiment of a ZMC2 antibody to human leptin-R in the presence of (excess) Leptin. On the x-axis different concentrations of leptin (ng/ml) are indicated (10000, 1000, 100, 10, 1, and 0.1 ng/ml) and ZMC2 in a concentration of 10 ng/ml). The y-axis shows the absorbance at 450 nm (OD 450 nm). As can be seen, the binding of ZMC2 to leptin-R is apparently very strong. Only a large excess of leptin can displace the binding of ZMC2 antibody to human leptin-R (cf. Example 4).

For a competitive binding experiment of a ZMC2 antibody to human leptin-R in the presence of (excess) leptin, an ELISA plate was coated with recombinant human leptin-R (200 ng/well). Different concentrations of leptin (10000, 1000, 100, 10, 1, 0,1 ng/ml) were added to wells in presence or absence of ZMC2 antibody. ZMC2, if added, was present in a concentration of 10 ng/ml. Binding of ZMC2 antibody was then subsequently detected using a biotinylated secondary antibody followed by SAV-HRP and the signal (OD of resulted colour) was measured at 450 nm. As can be obtained from FIG. 7 only a large excess of leptin can displace the binding of ZMC2 antibody to human leptin-R. Accordingly, binding of ZMC2 antibody to leptin-R is highly specific.

Example 5

Dose Response of Luciferase Activity in Response to Leptin Stimulation

Figure 8:
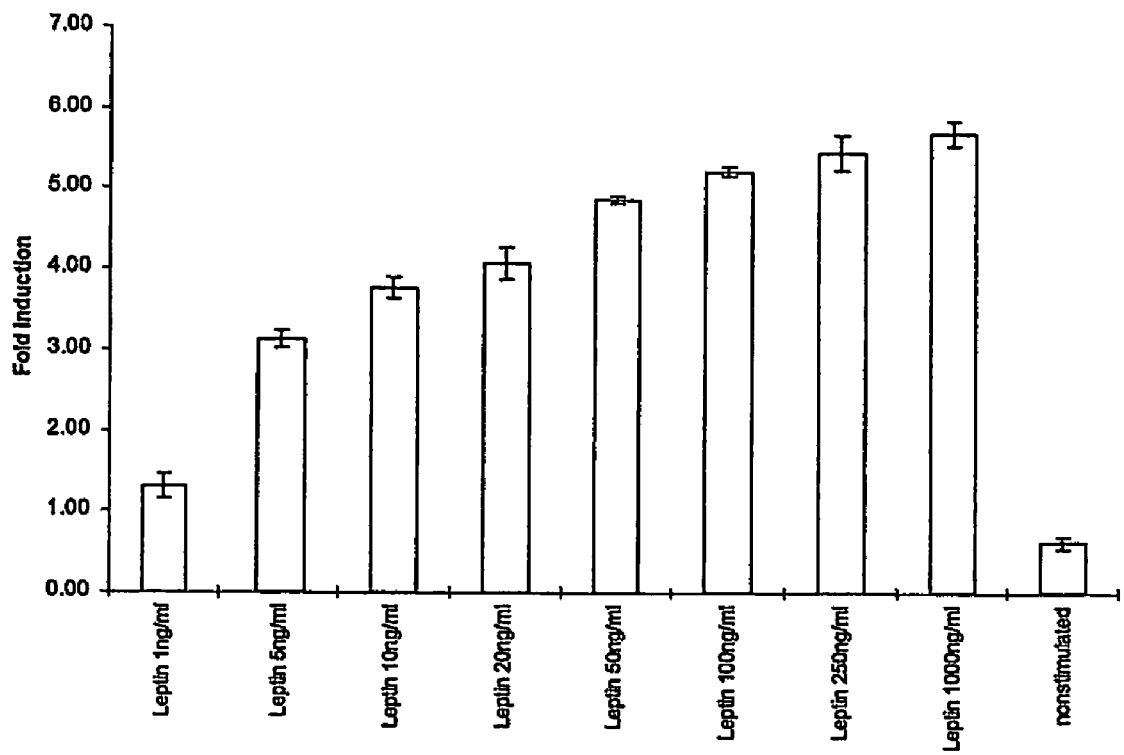
FIG. 8: shows a bar plot of the dose response of luciferase activity in response to leptin stimulation in HEK293 cells. Therefore, HEK293 cells were transiently transfected with Ob-Rb and a STAT3-luciferase reporter construct and stimulated with varying doses of leptin for 2 hours. Then, luciferase activity was measured and was corrected for B-galactosidase. On the x-axis different concentrations of leptin (ng/ml) are indicated (1, 5, 10, 20, 50, 100, 250, 1000 ng/ml). The y-axis shows the degree of fold induction versus unstimulated cells. As can be obtained from FIG. 8, induction of HEK293 cells with leptin reaches a maximum level, whereby nearly no further stimulation is observed (cf. Example 5).

In order to detect a dose response of luciferase activity in response to leptin stimulation, HEK293 cells were transiently transfected with leptin-Rb and a STAT3-luciferase reporter construct and stimulated with varying doses of leptin for 2 hours. After 2 hours the media were replaced with fresh medium containing no leptin and cultures were inoculated for further 4 hours before the cells were lysed. Subsequently, luciferase activity was measured and corrected for β-galactosidase, which was used as a transfection control. The results are shown in FIG. 8. The values shown express the fold induction over the unstimulated cells. The induction is dose dependent and reaches a maximum at about 50-1000 ng/ml Leptin.

Example 6

Dose Response for the Inhibitory Effects of ZMC2 Antibody On Leptin Signalling

Figure 9:
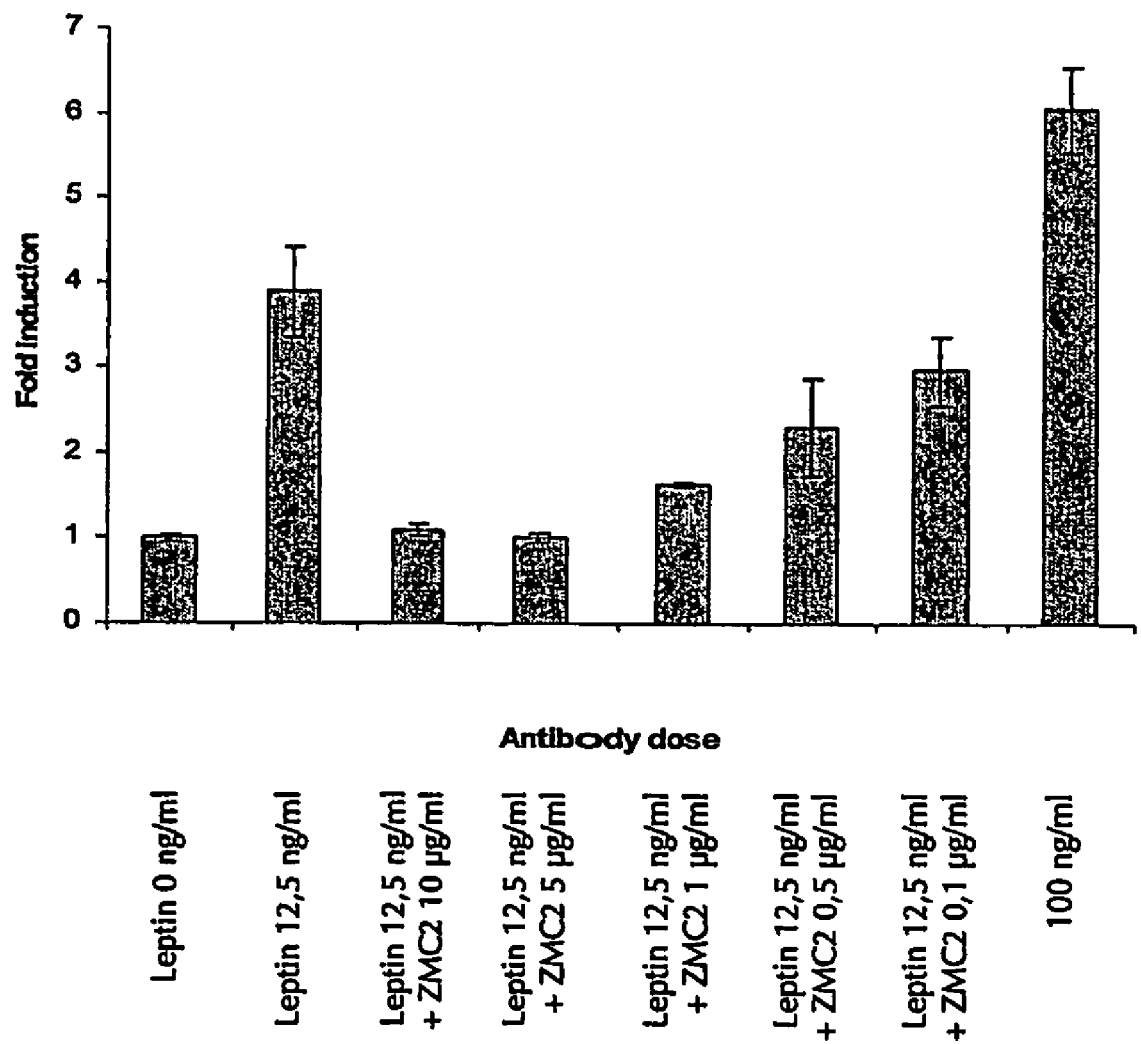
FIG. 9: illustrates in a bar plot the dose response for inhibitory effects of ZMC2 antibody on leptin signalling. HEK293 cells were transiently transfected with leptin-R and a STAT3-luciferase reporter construct and stimulated with leptin (5 ng/ml) for 2 hours. Different doses of ZMC2 antibody (ug/ml, see x-axis) were added to the culture, luciferase activity was measured and corrected for B-galactosidase. The results are expressed as fold induction over the unstimulated cells. On the x-axis different concentrations of leptin (ng/ml) (0, 12,5 and 100 ng/ml) and ZMC2 (10, 5, 1, 0,5, and 0,1 ng/ml) are indicated. As can be obtained from FIG. 9, ZMC2 antibody demonstrated inhibitory effects on leptin signalling in a dose response manner (cf. Example 6).

To obtain a dose response for the inhibitory effects of ZMC2 antibody on leptin signaling HEK293 cells were transiently transfected with leptin-Rb and a STAT3-luciferase reporter construct and stimulated with leptin (5 ng/ml) for 2 hours. Different doses of ZMC2 antibody (10, 5, 1, 0,5 and 0,1 µg/ml, if leptin is contained) were added to the culture 30 minutes prior to addition of leptin (0 ng/ml, if no ZMC2 is contained and 12,5 ng/ml, if ZMC2 is contained). Luciferase activity was measured subsequently and was corrected for β-galactosidase. The results are shown as a bar plot in FIG. 9, being expressed as fold induction over the unstimulated cells. As a result ZMC2 antibody demonstrated inhibitory effects on leptin signalling in a dose response manner.

Example 7

Binding of ZMC2 Antibody to Mouse Leptin-R

Figure 10:
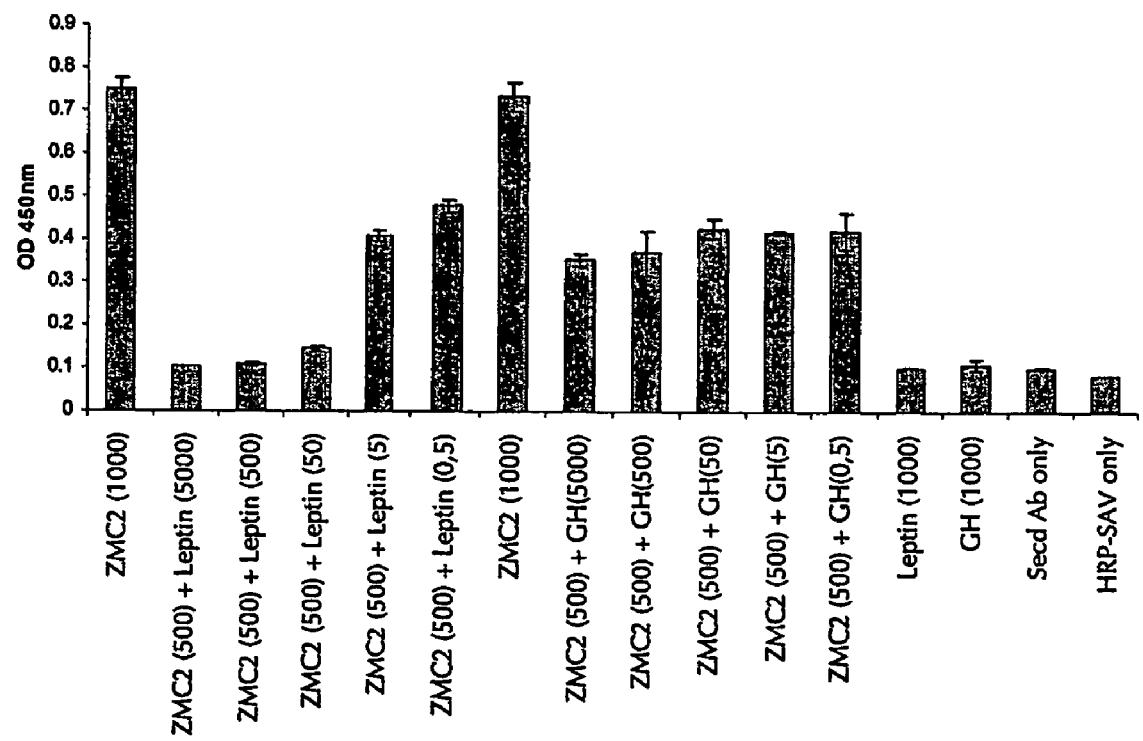
FIG. 10: shows a bar plot of the binding of ZMC2 antibody to mouse leptin-R. Binding of ZMC2 antibody was detected using a biotinylated secondary antibody followed by SAV-HRP. The OD of the resulted colour was measured at 450 nm. On the x-axis different concentrations of leptin (ng/ml) and ZMC2 (ng/ml) are indicated. As may bee seen in FIG. 10, ZMC2 antibody binds to mouse leptin-R in a dose dependent manner and its binding can be displaced by leptin at high concentrations of leptin only (cf. Example 7).

An ELISA plate was coated with recombinant mouse leptin-R (200 ng/well) and different concentrations of ZMC2 antibody, leptin, growth hormone or the combination of them (ng/ml) were added. Binding of ZMC2 antibody was detected using a biotinylated secondary antibody followed by SAV-HRP and the OD of resulted colour was measured at 450 nm. The results are shown in FIG. 10 as a bar plot. As can be obtained from the plot ZMC2 antibody binds to mouse leptin-R in a dose dependent manner and its binding can be displaced by leptin only at high doses.

Example 8

Blocking of TNF-α Production in Leptin Activated Human Monocytes by ZMC2

Figure 11:
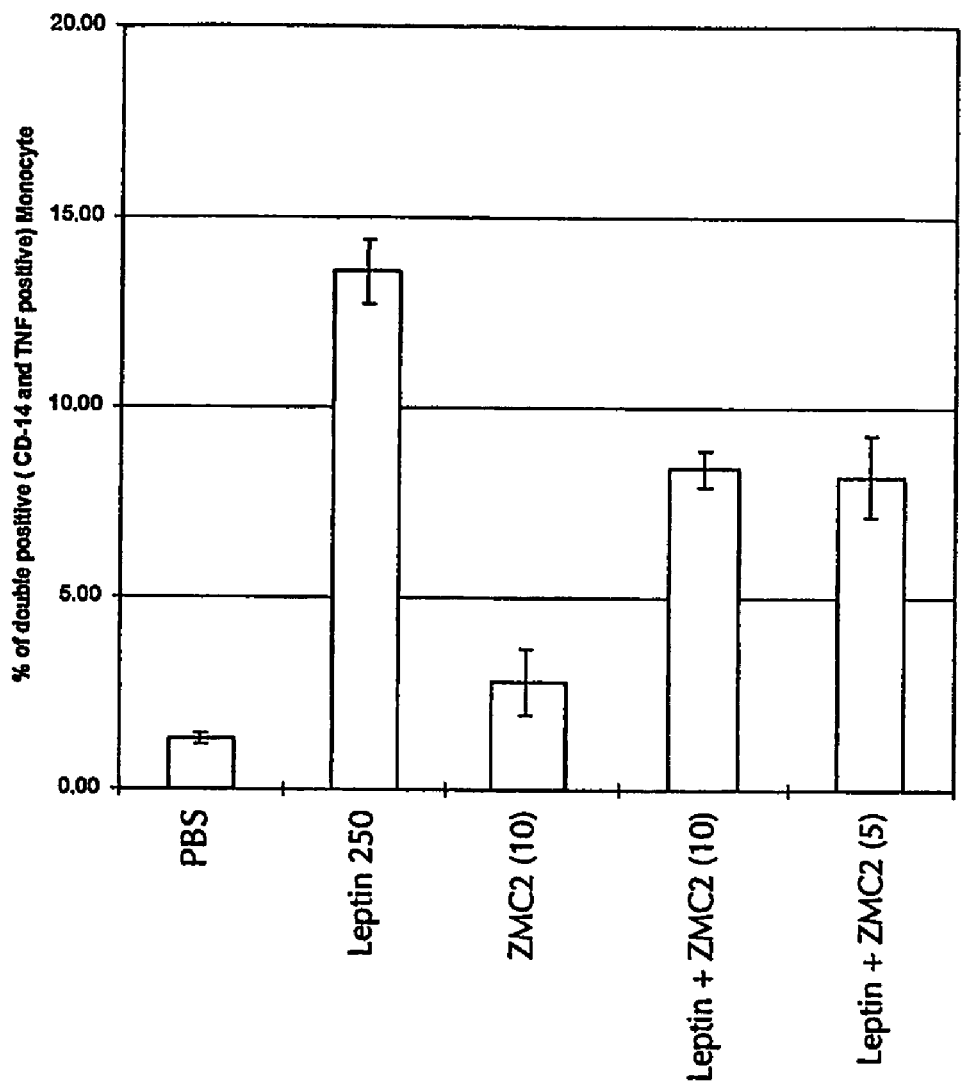
FIG. 11: illustrates in a bar plot the blocking of TNF-α production in leptin activated human monocytes by ZMC2 antibody. Human monocytes were cultured in the presence of PBS, Leptin (250 ng/ml), ZMC2 (10 ng/ml)+Leptin and ZMC2 (5 ng/ml)+Leptin. The Y axis shows percentage of monocytes expressing TNF-α (cf. Example 8).

For this experiment, TNF-α production was induced by leptin activated human monocytes. After inducing TNF-α production, ZMC2 (10 and 5 ng/ml) was added to the monocytes in the presence and absence of leptin (250 ng/ml). The results are shown in FIG. 11. As can be seen in FIG. 11, ZMC2 is capable of blocking TNF-α production by leptin activated human monocytes. Y axis shows percentage of monocytes expressing TNF-α (% double positive (CD-14 and TNF-α positive) monocytes).

Example 9

Stimulation of Human PBL in Autologous Human Serum by okt3 (Anti-CD3 Experiment)

For measuring the stimulation of human PBL in autologous human serum by okt3 (optimal dose 100 ng/ml) cells were inoculated in the presence of ZMC2 ab (from 0, 0.1, 1 and 10 ug/ml) and in the presence or absence of exogenous leptin (100 ng/ml). Cells were harvested after 60 min allowing maximum DNA synthesis. The proliferation was measured (cpm) and can be seen in FIG. 12A. There is a minor effect of ZMC2 to increase PBL proliferation that is reduced by leptin. This increase in proliferation can be reversed by leptin, as can be seen in the following experiments. ZMC2 thus acts as an antagonist. Furthermore, it is considered that the response to anti-CD3 stimulation in humans in the presence of leptin is dependent on the relative proportion of naive/memory cells in PBL; the more naive cells are present the greater is the increase in proliferation in response to leptin; alternatively, the more memory cells are present the greater is the inhibition of proliferation induced by leptin (although IFN-g secretion is increased, despite the reduced proliferation of memory cells).

Figure 12:
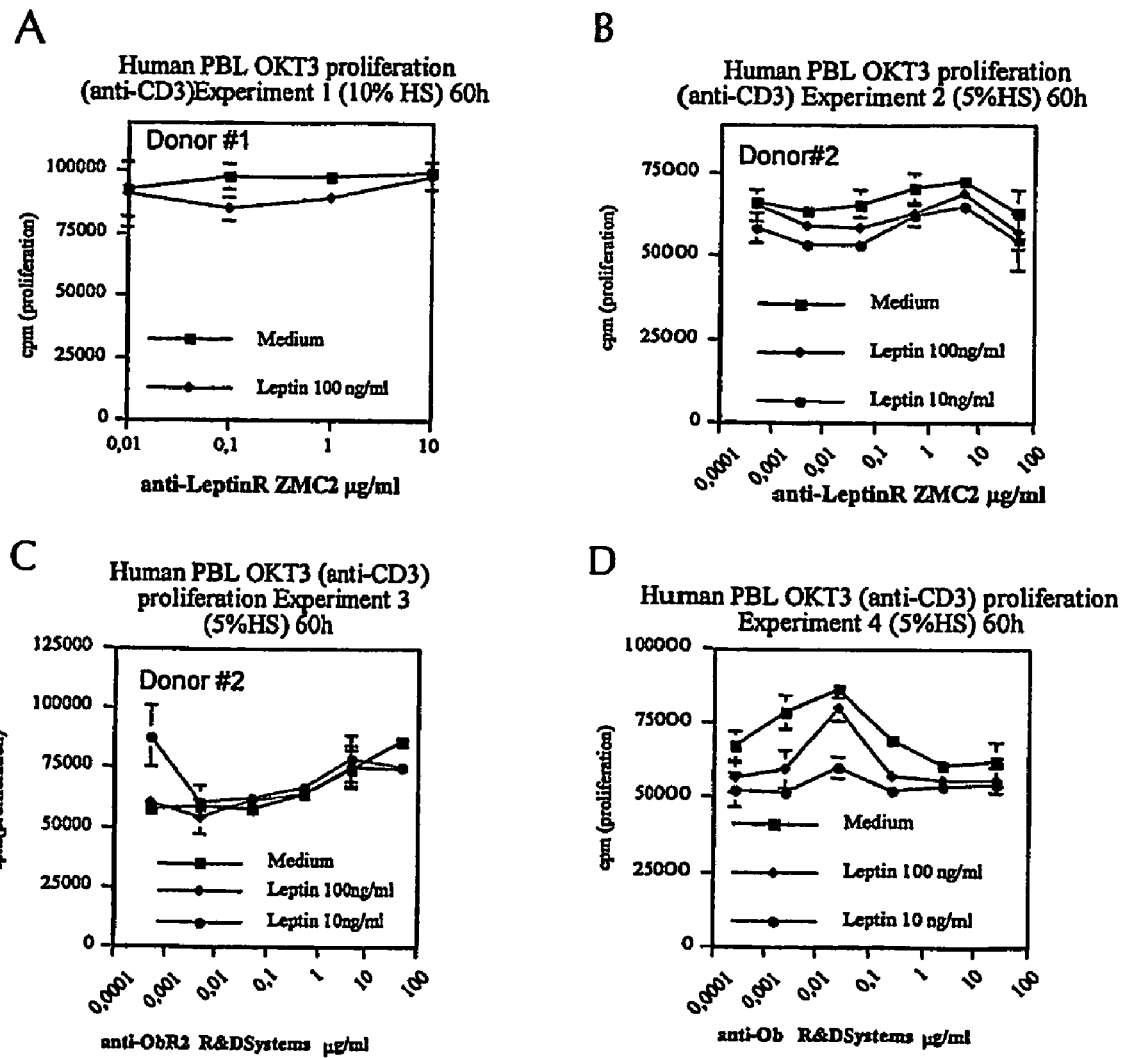
FIG. 12A depicts a proliferation assay showing the stimulation by okt3 (optimal dose 100 ng/ml) of human PBL in autologous human serum in the presence of ZMC2 ab in different concentrations.
FIG. 12B shows the stimulation by okt3 (optimal dose 100 ng/ml) of human PBL in autologous human serum with different doses of leptin and more points on ZMC2 mAb dose response (0, 0.005, 0.05, 0.5, 5, 50 ug/ml) are shown. The curve in FIG. 12B, is biphasic with a slight tendency to increased proliferation after treatment with ZMC2 which is again reduced by leptin (cf. Example 9).
FIGS. 12C-D: show comparative experiments carried out with a donor (in the same assay as shown for FIGS. 12A and B) with an agonistic anti-leptin receptor ab from R&D systems and another anti-human leptin treatment from R&Dsystems. The agonistic anti-ObR2 antibody increases proliferation in a similar fashion to the antagonistic ZMC2 and the anti-leptin at low doses increases the proliferation. The proliferation then is reversed by leptin when using ZMC2, whereas it is still stimulated with anti-ObR2. On a mixed population of naive/memory cells; with leptin present in serum controlling memory cell proliferation, the addition of the blocking ab ZMC2 thus slightly increases proliferation which can then be reversed. Thus, ZMC2 is acting as an antagonistic antibody (cf. Example 9).

In FIGS. 12B, C and D stimulation by okt3 (optimal dose 10 ng/ml) of human PBL in autologous human serum with different doses of leptin (10 and 100 ng/ml) and more points on ZMC2 mAb dose response (0,0001, 0,001, 0,01, 0,1, 1, 10, 100 ug/ml) is shown. As can be seen, the curve is biphasic with a slight tendency to increased proliferation after treatment with ZMC2 (FIG. 12B) which is again reduced by leptin; with donor 2 experiments were performed in the same assay, i.e. the agonistic anti-leptin receptor ab (anti-ObR2) from R&D systems (FIG. 12C) and another anti-human leptin treatment from R&D systems (FIG. 12D). anti-ObR2 increases proliferation in a similar fashion to ZMC2 and the anti-leptin at low doses increases the proliferation, which is reversed by leptin. Here, the effects on a mixed population of naive/memory cells are studied, wherein leptin is present in serum controlling memory cell proliferation. Addition of the blocking ab ZMC2 slightly increases proliferation, which can be reversed upon addition of leptin. Thus, ZMC2 is acting as an antagonistic antibody, whereas anti-ObR2 acts as an agonistic antibody.

Example 10

Elongated Proliferation Experiments

Figure 13:
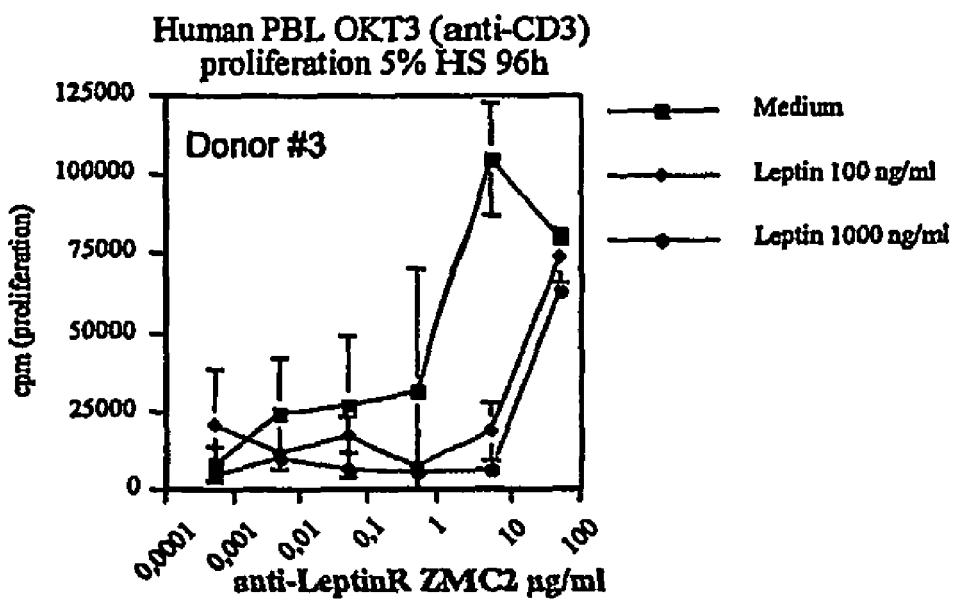
FIG. 13: shows a plot of the results from a proliferation assay similar to those as disclosed in FIG. 12, but extended to a longer time period (proliferation at 4 days (96 h)).

To better define the effect of ZMC2, proliferation experiments were carried out over a longer time period to see whether the increase in proliferation was more visible when cells were to be in a later phase of cell cycle. Therefore, proliferation was measured at 4 days (96 h), and surprisingly the ZMC2 ab still stimulated proliferation, wherein—looking at the overall response on a mixed T cell population—ZMC2 turned out to act as an antagonist, since addition of leptin reduces proliferation (see FIG. 13). The specificity of ZMC2 additionally can be measured by the fact that addition of leptin reduces proliferation.

Example 11

Food Uptake Experiments on ob/ob and ob/+ Mice: 3 Mice Group

Figure 14:
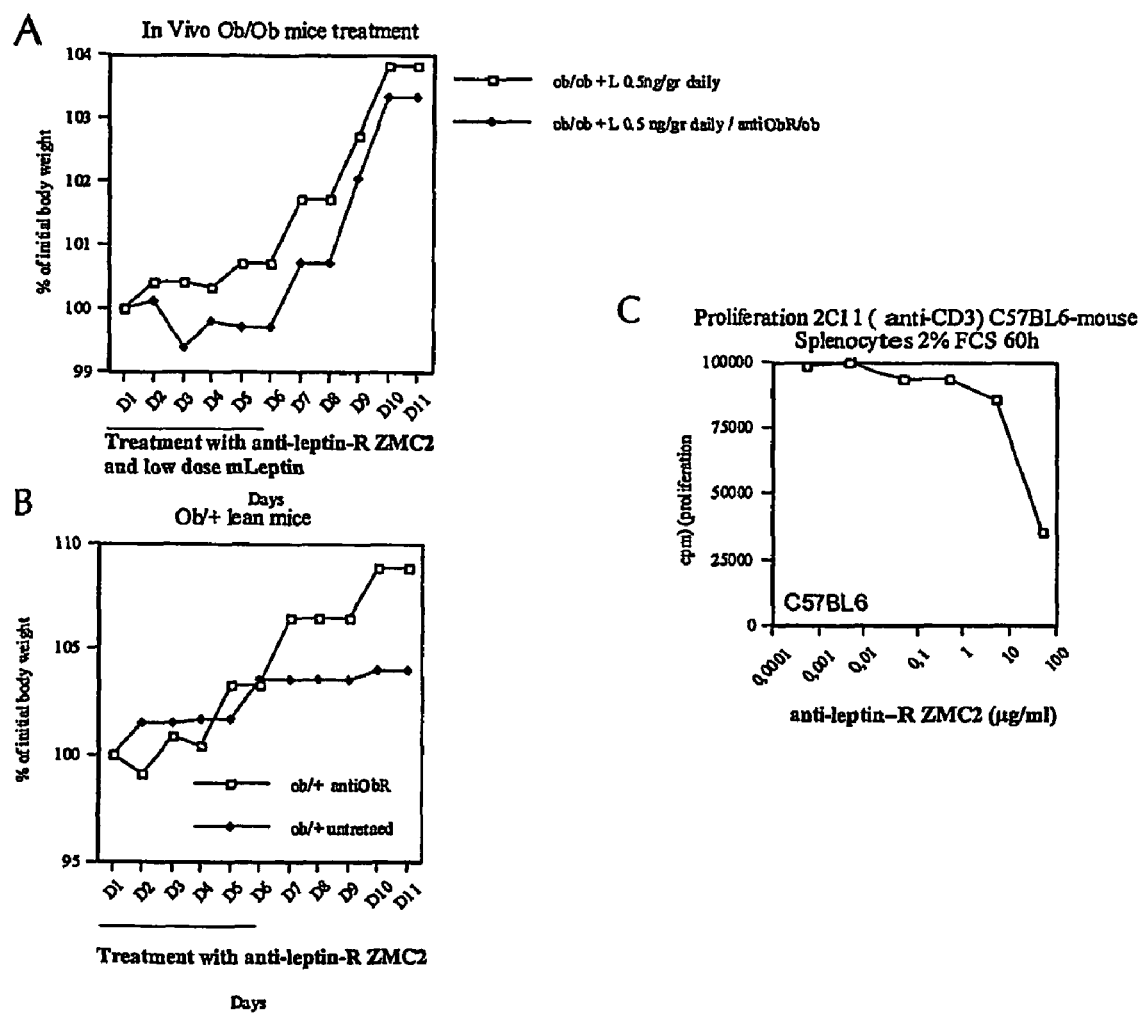
FIGS. 14A-C: show a plot of food uptake experiments (cf. Example 11) on ob/ob and ob/+ mice: 3 mice groups were selected; all females; The mice were initially treated with low dose leptin such as to keep the weight constant. The treatment was 100 ug/daily ip+Rec leptin 0.5 ug/gr weight, for 5 days.
Figure 16:
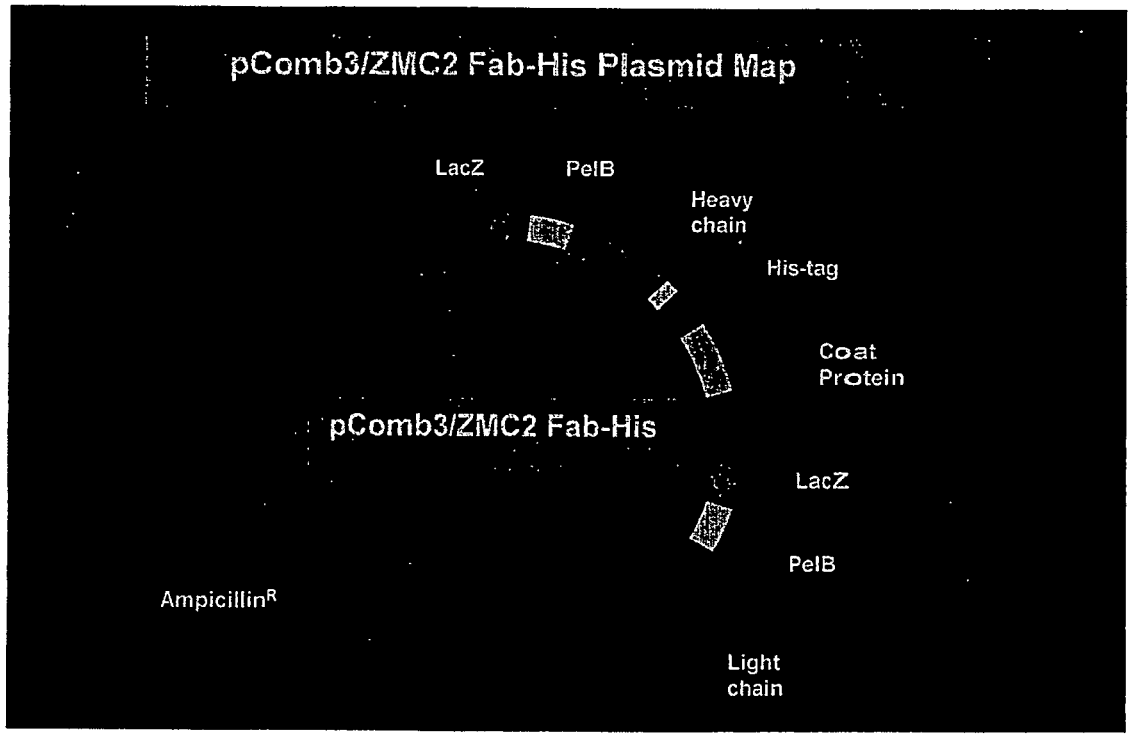
FIG. 16: shows a plasmid map of the pComb3/ZMC2 $F_{ab}$-His clone.
Figure 17:
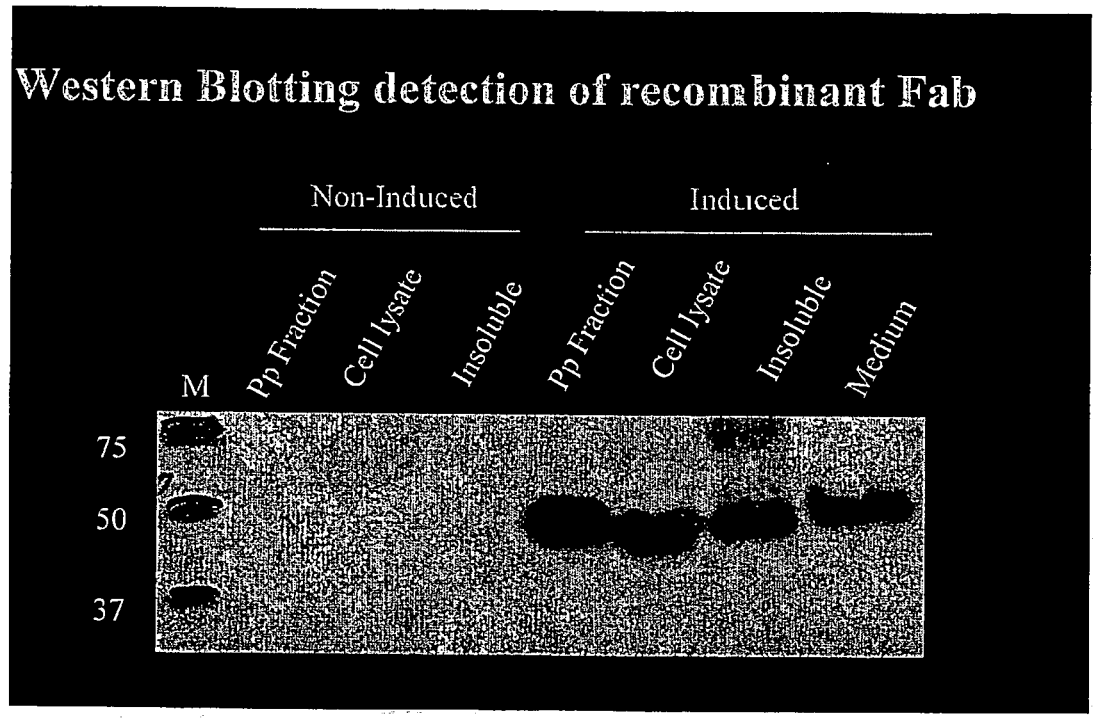
FIG. 17: shows the results of a Western Blot experiment during purification of recombinant $F_{ab}$ ZMC2. As can be obtained from the Western Blot, recombinant $F_{ab}$ ZMC2 is expressed in the soluble fraction and the Blot shows a protein of the correct size of Kappa light chain.
Figure 18:
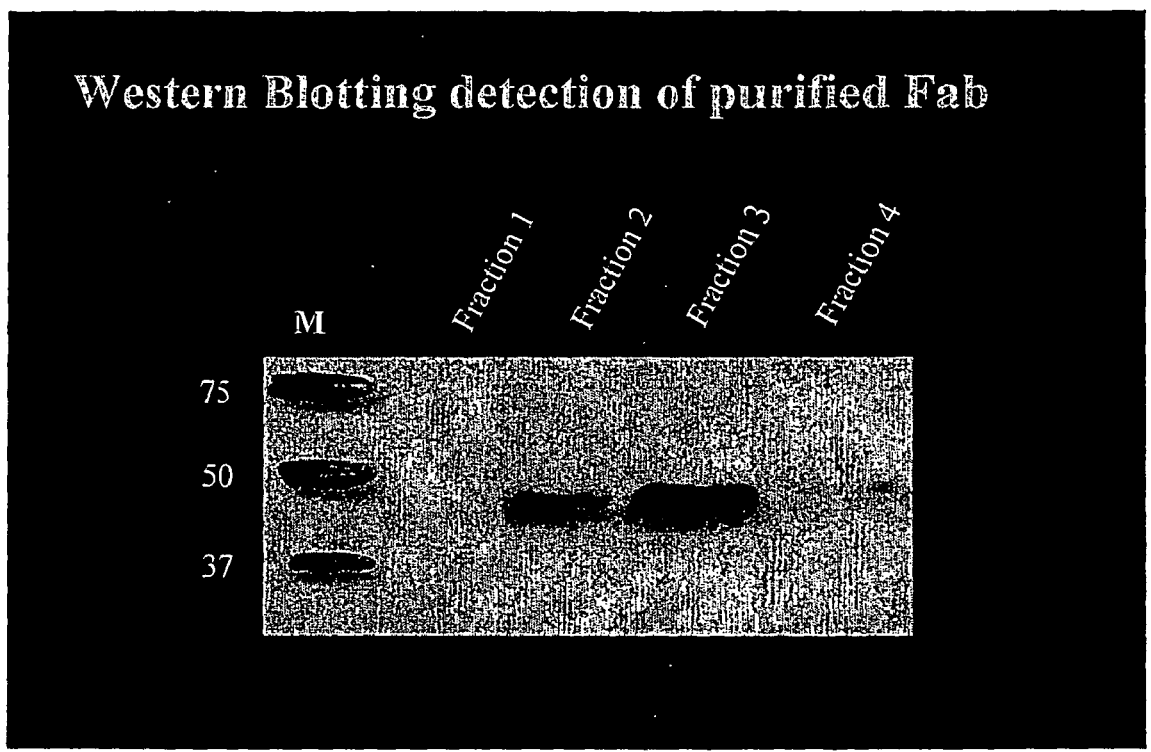
FIG. 18: shows the results of a Western Blot experiment during purification of recombinant His-tagged $F_{ab}$ ZMC2. As can be obtained from the Western Blot, His tagged $F_{ab}$ ZMC2 can be purified on a Cobalt Column.
Figure 19:
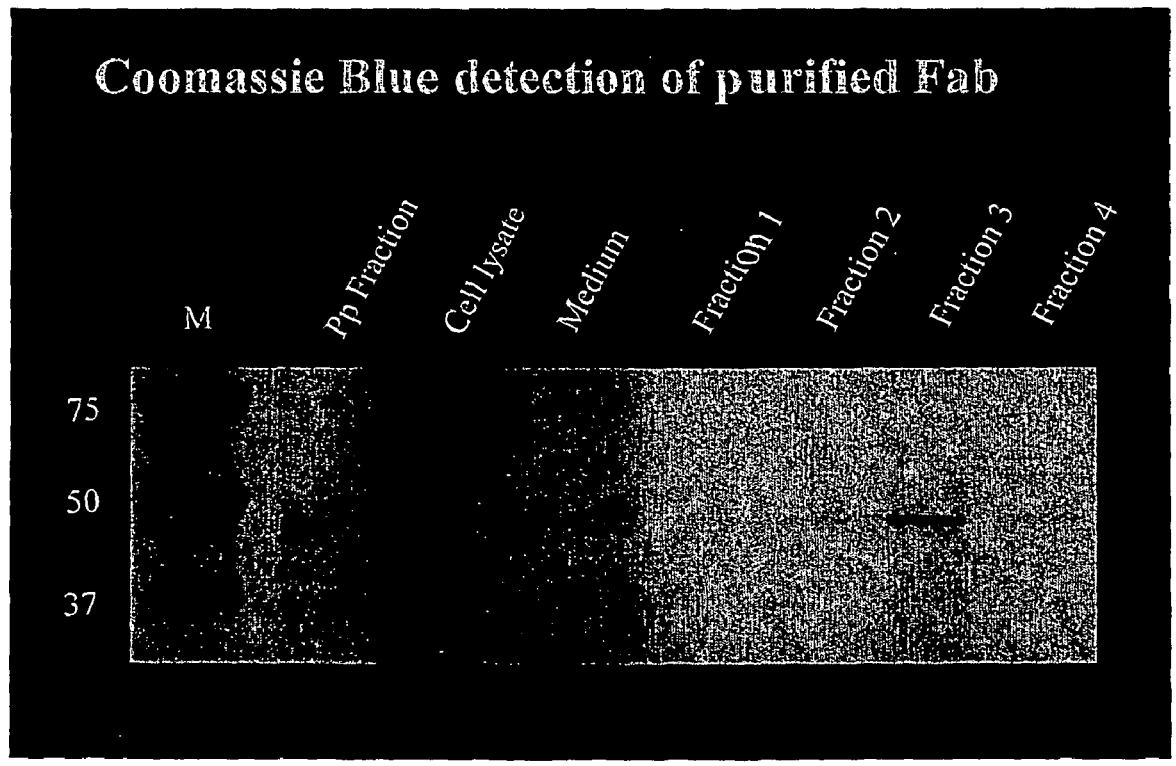
FIG. 19: shows a Coomassie Blue staining of a polyacrylamide gel of a purified $F_{ab}$ ZMC2 antibody.

For food uptake experiments ob/ob and ob/+ mice, all females, were taken. In case of ob/ob, mice were treated with low dose leptin in order to maintain weight, i.e. not to loose weight but also not to increase weight, as it usually happens. Usually 1 gram of body weight every 2 days is typically fed to the mice. The treatment in the experiment was 100 ug/daily ip+Rec leptin 0.5 ug/gr weight, for 5 days. As can be seen in FIG. 14A the curve in % in body weight change is flat during treatment with leptin alone, indicating that the treatment was working. Instead of being pre-vented by the ab, body weight was slightly increased in terms of no change in body weight. In an comparative Experiment heterozygous mice (see FIG. 14B), were used because they show a lower leptin than normal mice. The heterozygotes were treated in parallel with the same dose of ab alone. The untreated mice showed a tendency to increase body weight over the time (less strong than for the ob/ob mice); the ab treated were similar for body weight, but after stopping body weight increased more than the controls.

Proliferation of Spleen Cells from Normal Mouse (B6)

Proliferation of spleen cells from normal mouse (B6) was stimulated with anti-CD3 for mouse (called 2C11) (0,0001, 0,001, 0,01, 0,1, 1, 10, 100 ug/ml) dose response in the presence of FCS 2%. As can be seen in FIG. 14C, a clear inhibition can be obtained at 10-100 ug/ml.

The invention claimed is:

1. An antibody or a specific antigen-biding fragment thereof, wherein the antibody binds specifically to one or both of a leptin receptor and a leptin-binding protein, wherein the binding substantially reduces interaction of the leptin receptor or of the leptin-binding protein with its ligand, and wherein the antibody comprises an amino acid sequence of SEQ ID NO: 6 and the appropriate light chain.

2. The antibody according to claim 1, wherein the binding prevents interaction of the leptin receptor or of the leptin-binding protein with its ligand.

3. The antibody according to claim 1, which specifically binds to an extracellular domain of a leptin receptor, or of a leptin-binding protein.

4. The antibody according to one of claim 1, wherein the antibody binds to a ligand binding site of the leptin-binding protein.

5. The antibody according to claim 1, wherein the ligand is leptin.

6. The antibody according to claim 1, wherein the leptin-binding protein is solubilized or suspended in a bodily fluid.

7. The antibody according to claim 1, which is a monoclonal antibody.

8. The antibody according to claim 1, which is the antibody ZMC2.

9. The antibody according to claim 1, wherein the antibody is humanized.

10. The antibody according to claim 1, wherein the light chain comprises the amino acid sequence of SEQ ID NO:1.

11. An F(ab') 2 fragment or a single-chain antibody (scFv) of an antibody according to claim 1.

12. A pharmaceutical composition comprising an antibody or a specific antigen-biding fragment thereof according to claim 1.

13. A fusion protein comprising as a first portion an antibody according to claim 1 or a specific antigen-biding fragment thereof, and a second portion which is an antibody or a fragment thereof or a polypeptide.

14. The fusion protein according to claim 13, wherein the polypeptide is leptin.

15. The fusion protein according to claim 13, further comprising a linker between the first and the second portions.

16. The fusion protein according to claim 15, wherein the linker comprises about 5 to 40 amino acid residues, or about 5 to 30 amino acid residues, or about 5 to 20 amino acid residues.

17. The fusion protein according to claim 15, wherein the linker comprises at least 50%, or at least 60%, or at least 70% or at least 80% glycine.

18. The fusion protein according to claim 15, wherein the fusion protein is bispecific.

19. The fusion protein according to claim 18, wherein the fusion protein is specific to a leptin receptor or a leptin-binding protein as a first specificity, and to a cell surface protein as a second specificity.

20. The fusion protein according to claim 13, wherein the fusion protein comprises the amino acid sequence of SEQ ID NO: 8, or is encoded by the nucleic acid having a sequence SEQ ID NO:7.

* * * * *

SEQUENCE LISTING

<160> NUMBER OF SEQ ID NOS: 13

<210> SEQ ID NO 1
<211> LENGTH: 272
<212> TYPE: PRT
<213> ORGANISM: Mus musculus
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (239)..(240)
<223> OTHER INFORMATION: Xaa can be any naturally occurring amino acid
<220> FEATURE:
<221> NAME/KEY: misc_feature
<222> LOCATION: (246)..(246)
<223> OTHER INFORMATION: Xaa can be any naturally occurring amino acid
<220> FEATURE:
<221> NAME/KEY: misc_feature
<222> LOCATION: (249)..(249)
<223> OTHER INFORMATION: Xaa can be any naturally occurring amino acid
<220> FEATURE:
<221> NAME/KEY: misc_feature
<222> LOCATION: (261)..(261)
<223> OTHER INFORMATION: Xaa can be any naturally occurring amino acid

<400> SEQUENCE: 1

Xaa His Asn Pro Ile Pro Met Pro Pro Ala Ala Gly Leu Leu Leu
1               5                   10                  15

Leu Ala Ala Gln Pro Ala Met Ala Glu Leu Val Met Thr Gln Ser Pro
                20                  25                  30

Lys Phe Met Ser Thr Ser Ile Gly Asp Arg Val Asn Ile Thr Cys Lys
            35                  40                  45

Ala Thr Gln Asn Val Arg Thr Ala Val Thr Trp Tyr Gln Gln Lys Pro
        50                  55                  60

Gly Gln Ser Pro Gln Ala Leu Ile Phe Leu Ala Ser Asn Arg His Thr
65                  70                  75                  80

Gly Val Pro Ala Arg Phe Thr Gly Ser Gly Ser Gly Thr Asp Phe Thr
                85                  90                  95

Leu Thr Ile Asn Asn Val Lys Ser Glu Asp Leu Ala Asp Tyr Phe Cys
            100                 105                 110

Leu Gln His Trp Asn Tyr Pro Leu Thr Phe Gly Ser Gly Thr Lys Leu
        115                 120                 125

Glu Ile Lys Arg Ala Asp Ala Ala Pro Thr Val Ser Ile Phe Pro Pro
130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
210                 215                 220

Ser Thr Ser Pro Ile Val Lys Ser Phe Asn Arg Gly Glu Cys Xaa Xaa
225                 230                 235                 240

Ser Arg Val Lys Arg Xaa Gln Ser Xaa Gly Gly Pro Gly Thr Pro Ile
                245                 250                 255

```
Arg Pro Ile Gly Xaa Pro Tyr Tyr Asn Ser Leu Gly Gly Gly Phe Gln
              260                 265                 270
```

<210> SEQ ID NO 2
<211> LENGTH: 818
<212> TYPE: DNA
<213> ORGANISM: Mus musculus
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: CDS
<222> LOCATION: (3)..(818)
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (783)..(783)
<223> OTHER INFORMATION: n is a, c, g, or t
<220> FEATURE:
<221> NAME/KEY: misc_feature
<222> LOCATION: (818)..(818)
<223> OTHER INFORMATION: n is a, c, g, or t

<400> SEQUENCE: 2

```
na ngt cat aat cca ata cct atg cct acg gca gcc gct gga ttg tta       47
   Xaa His Asn Pro Ile Pro Met Pro Thr Ala Ala Ala Gly Leu Leu
    1               5                  10                  15 tta ctc gct gcc caa cca gcc atg gcc gag ctc gtg atg acc cag tct      95
Leu Leu Ala Ala Gln Pro Ala Met Ala Glu Leu Val Met Thr Gln Ser
             20                  25                  30 cca aaa ttc atg tcc aca tca ata gga gac agg gtc aat atc acc tgc     143
Pro Lys Phe Met Ser Thr Ser Ile Gly Asp Arg Val Asn Ile Thr Cys
         35                  40                  45 aag gcc act cag aat gtt cgt act gct gtt acc tgg tat caa cag aaa     191
Lys Ala Thr Gln Asn Val Arg Thr Ala Val Thr Trp Tyr Gln Gln Lys
     50                  55                  60 cca ggg cag tct cct caa gca ctg att ttc ttg gca tcc aac cgg cac     239
Pro Gly Gln Ser Pro Gln Ala Leu Ile Phe Leu Ala Ser Asn Arg His
 65                  70                  75 act ggt gtc cct gct cga ttc aca ggc agt gga tct ggg aca gat ttc     287
Thr Gly Val Pro Ala Arg Phe Thr Gly Ser Gly Ser Gly Thr Asp Phe
 80                  85                  90                  95 act ctc acc att aac aat gtg aaa tct gaa gac ctg gca gat tat ttc     335
Thr Leu Thr Ile Asn Asn Val Lys Ser Glu Asp Leu Ala Asp Tyr Phe
                100                 105                 110 tgt cta caa cat tgg aat tat cct ctc acg ttc ggc tcg ggg aca aag     383
Cys Leu Gln His Trp Asn Tyr Pro Leu Thr Phe Gly Ser Gly Thr Lys
            115                 120                 125 ttg gaa ata aaa cgg gct gat gct gca cca act gta tcc atc ttc cca     431
Leu Glu Ile Lys Arg Ala Asp Ala Ala Pro Thr Val Ser Ile Phe Pro
        130                 135                 140 cca tcc agt gag cag tta aca tct gga ggt gcc tca gtc gtg tgc ttc     479
Pro Ser Ser Glu Gln Leu Thr Ser Gly Gly Ala Ser Val Val Cys Phe
145                 150                 155 ttg aac aac ttc tac ccc aaa gac atc aat gtc aag tgg aag att gat     527
Leu Asn Asn Phe Tyr Pro Lys Asp Ile Asn Val Lys Trp Lys Ile Asp
160                 165                 170                 175 ggc agt gaa cga caa aat ggc gtc ctg aac agt tgg act gat cag gac     575
Gly Ser Glu Arg Gln Asn Gly Val Leu Asn Ser Trp Thr Asp Gln Asp
                180                 185                 190 agc aaa gac agc acc tac agc atg agc agc acc ctc acg ttg acc aag     623
Ser Lys Asp Ser Thr Tyr Ser Met Ser Ser Thr Leu Thr Leu Thr Lys
```

-continued

```
                195                     200                     205
gac gag tat gaa cga cat aac agc tat acc tgt gag gcc act cac aag    671
Asp Glu Tyr Glu Arg His Asn Ser Tyr Thr Cys Glu Ala Thr His Lys
        210                     215                     220 aca tca act tca ccc att gtc aag agc ttc aac agg gga gag tgt tag    719
Thr Ser Thr Ser Pro Ile Val Lys Ser Phe Asn Arg Gly Glu Cys
225                     230                     235 taa tct aga gtt aag cgg ccg caa tcg agg ggg ggc ccg gta ccc caa    767
    Ser Arg Val Lys Arg Pro Gln Ser Arg Gly Gly Pro Val Pro Gln
        240                     245                     250 ttc gcc cta tag ggg ngc cgt att aca att cac tgg gcg gcg gtt ttc    815
Phe Ala Leu     Gly Xaa Arg Ile Thr Ile His Trp Ala Ala Val Phe
255                     260                     265 aan                                                                818
Xaa
```

<210> SEQ ID NO 3
<211> LENGTH: 238
<212> TYPE: PRT
<213> ORGANISM: Mus musculus
<220> FEATURE:
<221> NAME/KEY: misc_feature
<222> LOCATION: (1)..(1)
<223> OTHER INFORMATION: The 'Xaa' at location 1 stands for Ser, Gly, Arg, or Cys.

<400> SEQUENCE: 3

```
Xaa His Asn Pro Ile Pro Met Pro Thr Ala Ala Gly Leu Leu Leu
1               5                   10                  15

Leu Ala Ala Gln Pro Ala Met Ala Glu Leu Val Met Thr Gln Ser Pro
                20                  25                  30

Lys Phe Met Ser Thr Ser Ile Gly Asp Arg Val Asn Ile Thr Cys Lys
                35                  40                  45

Ala Thr Gln Asn Val Arg Thr Ala Val Thr Trp Tyr Gln Gln Lys Pro
50                  55                  60

Gly Gln Ser Pro Gln Ala Leu Ile Phe Leu Ala Ser Asn Arg His Thr
65                  70                  75                  80

Gly Val Pro Ala Arg Phe Thr Gly Ser Gly Ser Gly Thr Asp Phe Thr
                85                  90                  95

Leu Thr Ile Asn Asn Val Lys Ser Glu Asp Leu Ala Asp Tyr Phe Cys
                100                 105                 110

Leu Gln His Trp Asn Tyr Pro Leu Thr Phe Gly Ser Gly Thr Lys Leu
                115                 120                 125

Glu Ile Lys Arg Ala Asp Ala Ala Pro Thr Val Ser Ile Phe Pro Pro
130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
                180                 185                 190

Lys Asp Ser Thr Tyr Ser Met Ser Ser Thr Leu Thr Leu Thr Lys Asp
                195                 200                 205

Glu Tyr Glu Arg His Asn Ser Tyr Thr Cys Glu Ala Thr His Lys Thr
                210                 215                 220

Ser Thr Ser Pro Ile Val Lys Ser Phe Asn Arg Gly Glu Cys
225                 230                 235
```

-continued

```
<210> SEQ ID NO 4
<211> LENGTH: 18
<212> TYPE: PRT
<213> ORGANISM: Mus musculus

<400> SEQUENCE: 4

Ser Arg Val Lys Arg Pro Gln Ser Arg Gly Gly Pro Val Pro Gln Phe
1               5                   10                  15

Ala Leu

<210> SEQ ID NO 5
<211> LENGTH: 13
<212> TYPE: PRT
<213> ORGANISM: Mus musculus
<220> FEATURE:
<221> NAME/KEY: misc_feature
<222> LOCATION: (2)..(2)
<223> OTHER INFORMATION: The 'Xaa' at location 2 stands for Ser, Gly,
      Arg, or Cys.
<220> FEATURE:
<221> NAME/KEY: misc_feature
<222> LOCATION: (13)..(13)
<223> OTHER INFORMATION: The 'Xaa' at location 13 stands for Lys, or
      Asn.

<400> SEQUENCE: 5

Gly Xaa Arg Ile Thr Ile His Trp Ala Ala Val Phe Xaa
1               5                   10

<210> SEQ ID NO 6
<211> LENGTH: 292
<212> TYPE: PRT
<213> ORGANISM: Mus musculus
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be any naturally occurring amino acid
<220> FEATURE:
<221> NAME/KEY: misc_feature
<222> LOCATION: (23)..(23)
<223> OTHER INFORMATION: Xaa can be any naturally occurring amino acid
<220> FEATURE:
<221> NAME/KEY: misc_feature
<222> LOCATION: (269)..(269)
<223> OTHER INFORMATION: Xaa can be any naturally occurring amino acid
<220> FEATURE:
<221> NAME/KEY: misc_feature
<222> LOCATION: (283)..(283)
<223> OTHER INFORMATION: Xaa can be any naturally occurring amino acid
<220> FEATURE:
<221> NAME/KEY: misc_feature
<222> LOCATION: (292)..(292)
<223> OTHER INFORMATION: Xaa can be any naturally occurring amino acid

<400> SEQUENCE: 6

Leu Ala Xaa Arg Gly Gly Gly Arg Lys Ile Xaa Phe Xaa Arg Glu Thr
1               5                   10                  15

Val Ile Met Lys Tyr Leu Xaa Ala Tyr Gly Pro Ala Ala Gly Leu Leu
                20                  25                  30

Leu Leu Ala Ala Gln Pro Ala Met Ala Gln Val Lys Leu Leu Glu Ser
        35                  40                  45

Gly Pro Gly Leu Val Ala Pro Ser Glu Ser Leu Ser Ile Thr Cys Thr
    50                  55                  60
```

```
Ile Ser Gly Phe Ser Leu Thr Asp Asp Gly Val Ser Trp Ile Arg Gln
 65                  70                  75                  80

Pro Pro Gly Lys Gly Leu Glu Trp Leu Gly Val Ile Trp Gly Gly Gly
                 85                  90                  95

Ser Thr Tyr Phe Asn Ser Leu Phe Lys Ser Arg Leu Ser Ile Thr Arg
            100                 105                 110

Asp Asn Ser Lys Ser Gln Val Phe Leu Glu Met Asp Ser Leu Gln Thr
        115                 120                 125

Asp Asp Thr Ala Met Tyr Tyr Cys Ala Lys His Asp Gly His Glu Thr
    130                 135                 140

Met Asp Tyr Trp Gly Gln Gly Thr Ser Val Thr Val Ser Ser Ser Lys
145                 150                 155                 160

Thr Thr Pro Pro Ser Val Tyr Pro Leu Ala Pro Gly Ser Ala Ala Gln
                165                 170                 175

Thr Asn Ser Met Val Thr Leu Gly Cys Leu Val Lys Gly Tyr Phe Pro
            180                 185                 190

Glu Pro Val Thr Val Thr Trp Asn Ser Gly Ser Leu Ser Ser Gly Val
        195                 200                 205

His Thr Phe Pro Ala Val Leu Gln Ser Asp Leu Tyr Thr Leu Ser Ser
    210                 215                 220

Ser Val Thr Val Pro Ser Ser Thr Trp Pro Ser Glu Thr Val Thr Cys
225                 230                 235                 240

Asn Val Ala His Pro Ala Ser Ser Thr Lys Val Asp Lys Lys Ile Val
                245                 250                 255

Pro Arg Asp Cys Thr Ser His His His His His Xaa Ala Ser Leu
            260                 265                 270

Val Val Ala Val Ala Leu His Ser Phe Val Xaa Ile Lys Ala Asn Arg
    275                 280                 285

Arg Pro Ala Xaa
    290

<210> SEQ ID NO 7
<211> LENGTH: 876
<212> TYPE: DNA
<213> ORGANISM: Mus musculus
<220> FEATURE:
<221> NAME/KEY: CDS
<222> LOCATION: (1)..(876)
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (31)..(31)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (848)..(848)
<223> OTHER INFORMATION: n is a, c, g, or t
<220> FEATURE:
<221> NAME/KEY: misc_feature
<222> LOCATION: (864)..(864)
<223> OTHER INFORMATION: n is a, c, g, or t
<220> FEATURE:
<221> NAME/KEY: misc_feature
```

<222> LOCATION: (873)..(873)
<223> OTHER INFORMATION: n is a, c, g, or t
<220> FEATURE:
<221> NAME/KEY: misc_feature
<222> LOCATION: (875)..(875)
<223> OTHER INFORMATION: n is a, c, g, or t

<400> SEQUENCE: 7

```
ttg gcc ncc cgc ggt ggc ggc cgc aaa att nta ttt nca agg gag aca        48
Leu Ala Xaa Arg Gly Gly Gly Arg Lys Ile Xaa Phe Xaa Arg Glu Thr
 1               5                  10                  15 gtc ata atg aaa tac ctt ttn gcc tac ggg cca gcc gct gga ttg tta        96
Val Ile Met Lys Tyr Leu Xaa Ala Tyr Gly Pro Ala Ala Gly Leu Leu
             20                  25                  30 tta ctc gct gcc caa cca gcc atg gcc cag gtg aaa ctg ctc gag tca       144
Leu Leu Ala Ala Gln Pro Ala Met Ala Gln Val Lys Leu Leu Glu Ser
         35                  40                  45 gga cct ggc ctg gtg gcg ccc tca gag agc ctg tcc atc aca tgc act       192
Gly Pro Gly Leu Val Ala Pro Ser Glu Ser Leu Ser Ile Thr Cys Thr
     50                  55                  60 atc tca ggg ttc tca tta acc gac gat ggt gta agc tgg att cgg cag       240
Ile Ser Gly Phe Ser Leu Thr Asp Asp Gly Val Ser Trp Ile Arg Gln
 65                  70                  75                  80 cct cca gga aag ggt ctg gag tgg ctg gga gta ata tgg ggt ggt gga       288
Pro Pro Gly Lys Gly Leu Glu Trp Leu Gly Val Ile Trp Gly Gly Gly
                 85                  90                  95 agc aca tac ttt aat tca ctt ttc aaa tcc aga ctg agc atc acc agg       336
Ser Thr Tyr Phe Asn Ser Leu Phe Lys Ser Arg Leu Ser Ile Thr Arg
            100                 105                 110 gac aac tct aag agc caa gtt ttc tta gaa atg gac agt cta caa act       384
Asp Asn Ser Lys Ser Gln Val Phe Leu Glu Met Asp Ser Leu Gln Thr
        115                 120                 125 gat gac aca gcc atg tac tac tgc gcc aaa cat gac gga cac gag act       432
Asp Asp Thr Ala Met Tyr Tyr Cys Ala Lys His Asp Gly His Glu Thr
    130                 135                 140 atg gac tat tgg ggt caa gga acc tca gtc acc gtc tcc tca tcc aaa       480
Met Asp Tyr Trp Gly Gln Gly Thr Ser Val Thr Val Ser Ser Ser Lys
145                 150                 155                 160 acg aca ccc cca tct gtc tat cca ctg gcc cct gga tct gct gcc caa       528
Thr Thr Pro Pro Ser Val Tyr Pro Leu Ala Pro Gly Ser Ala Ala Gln
                165                 170                 175 act aac tcc atg gtg acc ctg gga tgc ctg gtc aag ggc tat ttc cct       576
Thr Asn Ser Met Val Thr Leu Gly Cys Leu Val Lys Gly Tyr Phe Pro
            180                 185                 190 gag cca gtg aca gtg acc tgg aac tct gga tcc ctg tcc agc ggt gtg       624
Glu Pro Val Thr Val Thr Trp Asn Ser Gly Ser Leu Ser Ser Gly Val
        195                 200                 205 cac acc ttc cca gct gtc ctg cag tct gac ctc tac act ctg agc agc       672
His Thr Phe Pro Ala Val Leu Gln Ser Asp Leu Tyr Thr Leu Ser Ser
    210                 215                 220 tca gtg act gtc ccc tcc agc acc tgg ccc agc gag acc gtc acc tgc       720
Ser Val Thr Val Pro Ser Ser Thr Trp Pro Ser Glu Thr Val Thr Cys
225                 230                 235                 240 aac gtt gcc cac ccg gcc agc agc acc aag gtg gac aag aaa att gtg       768
Asn Val Ala His Pro Ala Ser Ser Thr Lys Val Asp Lys Lys Ile Val
                245                 250                 255 ccc agg gat tgt act agt cat cat cat cat cat taa gct agc cta           816
Pro Arg Asp Cys Thr Ser His His His His His     Ala Ser Leu
            260                 265                 270 gtg gtg gcg gtg gct ctc cat tcg ttt gtg ang ata aag gcc aat cgn       864
Val Val Ala Val Ala Leu His Ser Phe Val Xaa Ile Lys Ala Asn Arg
    275                 280                 285
```

-continued

```
aga cct gcn cna                                                    876
Arg Pro Ala Xaa
        290
```

<210> SEQ ID NO 8
<211> LENGTH: 268
<212> TYPE: PRT
<213> ORGANISM: Mus musculus
<220> FEATURE:
<221> NAME/KEY: misc_feature
<222> LOCATION: (3)..(3)
<223> OTHER INFORMATION: The 'Xaa' at location 3 stands for Thr, Ala,
      Pro, or Ser.
<220> FEATURE:
<221> NAME/KEY: misc_feature
<222> LOCATION: (11)..(11)
<223> OTHER INFORMATION: The 'Xaa' at location 11 stands for Ile, Val,
      or Leu.
<220> FEATURE:
<221> NAME/KEY: misc_feature
<222> LOCATION: (13)..(13)
<223> OTHER INFORMATION: The 'Xaa' at location 13 stands for Thr, Ala,
      Pro, or Ser.
<220> FEATURE:
<221> NAME/KEY: misc_feature
<222> LOCATION: (23)..(23)
<223> OTHER INFORMATION: The 'Xaa' at location 23 stands for Leu, or
      Phe.

<400> SEQUENCE: 8

```
Leu Ala Xaa Arg Gly Gly Gly Arg Lys Ile Xaa Phe Xaa Arg Glu Thr
 1               5                  10                  15

Val Ile Met Lys Tyr Leu Xaa Ala Tyr Gly Pro Ala Ala Gly Leu Leu
            20                  25                  30

Leu Leu Ala Ala Gln Pro Ala Met Ala Gln Val Lys Leu Leu Glu Ser
        35                  40                  45

Gly Pro Gly Leu Val Ala Pro Ser Glu Ser Leu Ser Ile Thr Cys Thr
    50                  55                  60

Ile Ser Gly Phe Ser Leu Thr Asp Asp Gly Val Ser Trp Ile Arg Gln
65                  70                  75                  80

Pro Pro Gly Lys Gly Leu Glu Trp Leu Gly Val Ile Trp Gly Gly Gly
                85                  90                  95

Ser Thr Tyr Phe Asn Ser Leu Phe Lys Ser Arg Leu Ser Ile Thr Arg
            100                 105                 110

Asp Asn Ser Lys Ser Gln Val Phe Leu Glu Met Asp Ser Leu Gln Thr
        115                 120                 125

Asp Asp Thr Ala Met Tyr Tyr Cys Ala Lys His Asp Gly His Glu Thr
    130                 135                 140

Met Asp Tyr Trp Gly Gln Gly Thr Ser Val Thr Val Ser Ser Ser Lys
145                 150                 155                 160

Thr Thr Pro Pro Ser Val Tyr Pro Leu Ala Pro Gly Ser Ala Ala Gln
                165                 170                 175

Thr Asn Ser Met Val Thr Leu Gly Cys Leu Val Lys Gly Tyr Phe Pro
            180                 185                 190

Glu Pro Val Thr Val Thr Trp Asn Ser Gly Ser Leu Ser Ser Gly Val
        195                 200                 205

His Thr Phe Pro Ala Val Leu Gln Ser Asp Leu Tyr Thr Leu Ser Ser
    210                 215                 220

Ser Val Thr Val Pro Ser Ser Thr Trp Pro Ser Glu Thr Val Thr Cys
225                 230                 235                 240

Asn Val Ala His Pro Ala Ser Ser Thr Lys Val Asp Lys Lys Ile Val
                245                 250                 255
```

Pro Arg Asp Cys Thr Ser His His His His His His
            260                 265

<210> SEQ ID NO 9
<211> LENGTH: 23
<212> TYPE: PRT
<213> ORGANISM: Mus musculus
<220> FEATURE:
<221> NAME/KEY: misc_feature
<222> LOCATION: (14)..(14)
<223> OTHER INFORMATION: The 'Xaa' at location 14 stands for Lys, Arg,
      Thr, or Met.
<220> FEATURE:
<221> NAME/KEY: misc_feature
<222> LOCATION: (23)..(23)
<223> OTHER INFORMATION: The 'Xaa' at location 23 stands for Gln, Arg,
      Pro, or Leu.

<400> SEQUENCE: 9

Ala Ser Leu Val Val Ala Val Ala Leu His Ser Phe Val Xaa Ile Lys
1               5                   10                  15

Ala Asn Arg Arg Pro Ala Xaa
            20

<210> SEQ ID NO 10
<211> LENGTH: 832
<212> TYPE: DNA
<213> ORGANISM: Mus musculus
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (8)..(8)
<223> OTHER INFORMATION: n is a, c, g, or t
<220> FEATURE:
<221> NAME/KEY: CDS
<222> LOCATION: (38)..(814)

<400> SEQUENCE: 10
atnctttntt gttcctttct atgcggccca gccggcc atg gcc cag gtc cag ctg         55
                                        Met Ala Gln Val Gln Leu
                                        1               5 cag gag tca gga act gaa gtg gta aag cct ggg gct tca gtg aag ttg        103
Gln Glu Ser Gly Thr Glu Val Val Lys Pro Gly Ala Ser Val Lys Leu
        10                  15                  20 tcc tgc aag gct tct ggc tac atc ttc aca agt tat gat ata gac tgg        151
Ser Cys Lys Ala Ser Gly Tyr Ile Phe Thr Ser Tyr Asp Ile Asp Trp
    25                  30                  35 gtg agg cag acg cct gaa cag gga ctt gag tgg att gga tgg att ttt        199
Val Arg Gln Thr Pro Glu Gln Gly Leu Glu Trp Ile Gly Trp Ile Phe
40                  45                  50 cct gga gag ggg agt act gaa tac aat gag aag ttc aag ggc agg gcc        247
Pro Gly Glu Gly Ser Thr Glu Tyr Asn Glu Lys Phe Lys Gly Arg Ala
55                  60                  65                  70 aca ctg agt gta gac aag tcc tcc agc aca gcc tat atg gag ctc act        295
Thr Leu Ser Val Asp Lys Ser Ser Ser Thr Ala Tyr Met Glu Leu Thr
                75                  80                  85 agg ctg aca tct gag gac tct gct gtc tat ttc tgt gct aga ggg gac        343
Arg Leu Thr Ser Glu Asp Ser Ala Val Tyr Phe Cys Ala Arg Gly Asp
            90                  95                  100 tac tat agg cgc tac ttt gac ttg tgg ggc caa ggg acc acg gtc acc        391
Tyr Tyr Arg Arg Tyr Phe Asp Leu Trp Gly Gln Gly Thr Thr Val Thr
        105                 110                 115 gtc tcc tca tgt gga ggc ggt tca ggc gga ggt ggc tct ggc ggt ggc        439

```
                                                        -continued

Val Ser Ser Cys Gly Gly Ser Gly Gly Gly Ser Gly Gly Gly
    120             125             130 gga tct gac att gag ctc acc cag tct cca gca atc atg tct gca tct   487
Gly Ser Asp Ile Glu Leu Thr Gln Ser Pro Ala Ile Met Ser Ala Ser
135                 140                 145                 150 cca ggg gag agg gtc acc atg acc tgc agt gcc agc tca agt ata cgt   535
Pro Gly Glu Arg Val Thr Met Thr Cys Ser Ala Ser Ser Ser Ile Arg
                155                 160                 165 tac ata tat tgg tac caa cag aag cct gga tcc tcc ccc aga ctc ctg   583
Tyr Ile Tyr Trp Tyr Gln Gln Lys Pro Gly Ser Ser Pro Arg Leu Leu
            170                 175                 180 att tat gac aca tcc aac gtg gct cct gga gtc cct ttt cgc ttc agt   631
Ile Tyr Asp Thr Ser Asn Val Ala Pro Gly Val Pro Phe Arg Phe Ser
        185                 190                 195 ggc agt ggg tct ggg acc tct tat tct ctc aca atc aac cga atg gag   679
Gly Ser Gly Ser Gly Thr Ser Tyr Ser Leu Thr Ile Asn Arg Met Glu
    200                 205                 210 gct gag gat gct gcc act tat tac tgc cag gag tgg agt ggt tat cct   727
Ala Glu Asp Ala Ala Thr Tyr Tyr Cys Gln Glu Trp Ser Gly Tyr Pro
215                 220                 225                 230 ctc acg ttc ggc tcg ggc acc aag cgg gaa atc aaa cgg gcg gcc gca   775
Leu Thr Phe Gly Ser Gly Thr Lys Arg Glu Ile Lys Arg Ala Ala Ala
                235                 240                 245 ggt gcg ccg gtg ccg tat ccg gat ccg ctg gaa ccg cgt gccgcataga   824
Gly Ala Pro Val Pro Tyr Pro Asp Pro Leu Glu Pro Arg
            250                 255 ctgttgaa                                                           832

<210> SEQ ID NO 11
<211> LENGTH: 259
<212> TYPE: PRT
<213> ORGANISM: Mus musculus

<400> SEQUENCE: 11

Met Ala Gln Val Gln Leu Gln Glu Ser Gly Thr Glu Val Val Lys Pro
1               5                   10                  15

Gly Ala Ser Val Lys Leu Ser Cys Lys Ala Ser Gly Tyr Ile Phe Thr
            20                  25                  30

Ser Tyr Asp Ile Asp Trp Val Arg Gln Thr Pro Glu Gln Gly Leu Glu
        35                  40                  45

Trp Ile Gly Trp Ile Phe Pro Gly Glu Gly Ser Thr Glu Tyr Asn Glu
    50                  55                  60

Lys Phe Lys Gly Arg Ala Thr Leu Ser Val Asp Lys Ser Ser Ser Thr
65                  70                  75                  80

Ala Tyr Met Glu Leu Thr Arg Leu Thr Ser Glu Asp Ser Ala Val Tyr
                85                  90                  95

Phe Cys Ala Arg Gly Asp Tyr Tyr Arg Arg Tyr Phe Asp Leu Trp Gly
            100                 105                 110

Gln Gly Thr Thr Val Thr Val Ser Cys Gly Gly Gly Ser Gly Gly
        115                 120                 125

Gly Gly Ser Gly Gly Gly Ser Asp Ile Glu Leu Thr Gln Ser Pro
    130                 135                 140

Ala Ile Met Ser Ala Ser Pro Gly Glu Arg Val Thr Met Thr Cys Ser
145                 150                 155                 160

Ala Ser Ser Ser Ile Arg Tyr Ile Tyr Trp Tyr Gln Gln Lys Pro Gly
                165                 170                 175

Ser Ser Pro Arg Leu Leu Ile Tyr Asp Thr Ser Asn Val Ala Pro Gly
            180                 185                 190
```

```
Val Pro Phe Arg Phe Ser Gly Ser Gly Ser Gly Thr Ser Tyr Ser Leu
        195                 200                 205

Thr Ile Asn Arg Met Glu Ala Glu Asp Ala Ala Thr Tyr Tyr Cys Gln
        210                 215                 220

Glu Trp Ser Gly Tyr Pro Leu Thr Phe Gly Ser Gly Thr Lys Arg Glu
225                 230                 235                 240

Ile Lys Arg Ala Ala Ala Gly Ala Pro Val Pro Tyr Pro Asp Pro Leu
                245                 250                 255

Glu Pro Arg
```

<210> SEQ ID NO 12
<211> LENGTH: 1252
<212> TYPE: DNA
<213> ORGANISM: Mus musculus

<400> SEQUENCE: 12

```
tcgctgccca accagccatg cccaggtgaa aactgctcga gtcaggacct ggcctggtgg      60
cgccctcaga gagcctgtcc atcacatgca ctatctcagg ttctcattaa ccgacgatg     120
gtgtaagctg gattcggcag cctccaggaa agggtctgga gtggctggga gtaatatggg    180
gtggtggaag cacatacttt aattcacttt tcaaatccag actgagcatc accagggaca    240
actctaagag ccaagttttc ttagaaatgg acagtctaca aactgatgac acagccatgt    300
actactgcgc caaacatgac ggacacgaga ctatggacta ttggggtcaa ggaacctcag    360
tcaccgtctc ctcatccaaa acgacacccc catctgtcta tccactgccc ctggatctg     420
ctgcccaaac taactccatg gtgaccctgg atgcctggt caagggctat ttccctgagc     480
cagtgacagt gacctggaac tctggatccc tgtccagcgg tgtgcacacc ttcccagctg    540
tcctgcagtc tgacctctac actctgagca gctcagtgac tgtccctcc agcacctggc    600
ccagcgagac cgtcacctgc aacgttgccc accggccag cagcaccaag gtggacaaga    660
aaattgtgcc cagggattgt actagtggtg gcggaggtag tggtggcgga gtagcggtg    720
gcggaggttc tggtggcgga ggttccgaat tcctcgaggt gcccatccaa aaagtccaag    780
atgacaccaa aaccctcatc aagacaattg tcaccaggat caatgacatt tcacacacgc    840
agtcagtctc ctccaaacag aaagtcaccg gtttggactt cattcctggg ctccacccca    900
tcctgacctt atccaagatg gaccagacac tggcagtcta ccaacagatc ctcaccagta    960
tgccttccag aaacgtgatc caaatatcca acgacctgga gaacctccgg gatcttcttc   1020
acgtgctggc cttctctaag agctgccact tgccctggc cagtggcctg gagaccttgg    1080
acagcctggg gggtgtcctg gaagcttcag gctactccac agaggtggtg gccctgagca    1140
ggctgcaggg gtctctgcag gacatgctgt ggcagctgga cctcagccct gggtgcacta    1200
gtcatcatca tcatcatcat taagctagcc tagtggtggc ggtggctctc ca           1252
```

<210> SEQ ID NO 13
<211> LENGTH: 401
<212> TYPE: PRT
<213> ORGANISM: Mus musculus

<400> SEQUENCE: 13

```
Met Ala Gln Val Lys Leu Leu Glu Ser Gly Pro Gly Leu Val Ala Pro
1               5                   10                  15

Ser Glu Ser Leu Ser Ile Thr Cys Thr Ile Ser Gly Phe Ser Leu Thr
                20                  25                  30

Asp Asp Gly Val Ser Trp Ile Arg Gln Pro Pro Gly Lys Gly Leu Glu
```

```
            35                  40                  45
Trp Leu Gly Val Ile Trp Gly Gly Ser Thr Tyr Phe Asn Ser Leu
 50                  55                  60

Phe Lys Ser Arg Leu Ser Ile Thr Arg Asp Asn Ser Lys Ser Gln Val
 65                  70                  75                  80

Phe Leu Glu Met Asp Ser Leu Gln Thr Asp Thr Ala Met Tyr Tyr
                 85                  90                  95

Cys Ala Lys His Asp Gly His Glu Thr Met Asp Tyr Trp Gly Gln Gly
                100                 105                 110

Thr Ser Val Thr Val Ser Ser Ser Lys Thr Thr Pro Pro Ser Val Tyr
                115                 120                 125

Pro Leu Ala Pro Gly Ser Ala Ala Gln Thr Asn Ser Met Val Thr Leu
130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Val Thr Val Pro Ser Ser
                180                 185                 190

Thr Trp Pro Ser Glu Thr Val Thr Cys Asn Val Ala His Pro Ala Ser
                195                 200                 205

Ser Thr Lys Val Asp Lys Lys Ile Val Pro Arg Asp Cys Thr Ser Gly
210                 215                 220

Gly Gly Gly Ser Gly Gly Gly Gly Ser Gly Gly Gly Gly Ser Gly Gly
225                 230                 235                 240

Gly Gly Ser Glu Phe Leu Glu Val Pro Ile Gln Lys Val Gln Asp Asp
                245                 250                 255

Thr Lys Thr Leu Ile Lys Thr Ile Val Thr Arg Ile Asn Asp Ile Ser
                260                 265                 270

His Thr Gln Ser Val Ser Ser Lys Gln Lys Val Thr Gly Leu Asp Phe
                275                 280                 285

Ile Pro Gly Leu His Pro Ile Leu Thr Leu Ser Lys Met Asp Gln Thr
                290                 295                 300

Leu Ala Val Tyr Gln Gln Ile Leu Thr Ser Met Pro Ser Arg Asn Val
305                 310                 315                 320

Ile Gln Ile Ser Asn Asp Leu Glu Asn Leu Arg Asp Leu Leu His Val
                325                 330                 335

Leu Ala Phe Ser Lys Ser Cys His Leu Pro Trp Ala Ser Gly Leu Glu
                340                 345                 350

Thr Leu Asp Ser Leu Gly Gly Val Leu Glu Ala Ser Gly Tyr Ser Thr
                355                 360                 365

Glu Val Val Ala Leu Ser Arg Leu Gln Gly Ser Leu Gln Asp Met Leu
                370                 375                 380

Trp Gln Leu Asp Leu Ser Pro Gly Cys Thr Ser His His His His
385                 390                 395                 400

His
```